(12) United States Patent
Nagata et al.

(10) Patent No.: US 9,453,835 B2
(45) Date of Patent: Sep. 27, 2016

(54) METHOD FOR SCREENING A MODULATOR OF A TMEM16 FAMILY MEMBER

(71) Applicant: Kyoto University, Kyoto (JP)

(72) Inventors: Shigekazu Nagata, Kyoto (JP); Jun Suzuki, Kyoto (JP); Toshihiro Fujii, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/394,320

(22) PCT Filed: Apr. 16, 2013

(86) PCT No.: PCT/JP2013/061699
§ 371 (c)(1),
(2) Date: Oct. 14, 2014

(87) PCT Pub. No.: WO2013/157652
PCT Pub. Date: Oct. 24, 2013

(65) Prior Publication Data
US 2015/0079599 A1    Mar. 19, 2015

Related U.S. Application Data

(60) Provisional application No. 61/624,491, filed on Apr. 16, 2012.

(51) Int. Cl.
*C12Q 1/68* (2006.01)
*G01N 33/50* (2006.01)
*C12Q 1/34* (2006.01)
*G01N 33/92* (2006.01)

(52) U.S. Cl.
CPC ............. *G01N 33/5023* (2013.01); *C12Q 1/34* (2013.01); *G01N 33/5008* (2013.01); *G01N 33/92* (2013.01); *G01N 2500/00* (2013.01); *G01N 2500/04* (2013.01)

(58) Field of Classification Search
CPC ............... C12Q 1/34; G01N 33/5008; G01N 2500/00; G01N 33/5023; G01N 2500/04; G01N 33/92
See application file for complete search history.

(56) References Cited

U.S. PATENT DOCUMENTS

| | | | |
|---|---|---|---|
| 2002/0137905 A1* | 9/2002 | Sims ..................... | C07K 14/47 536/23.1 |
| 2009/0208946 A1* | 8/2009 | Moyer ................. | C12Q 1/6883 435/6.12 |
| 2012/0214742 A1* | 8/2012 | Lee ........................ | A61K 31/00 514/17.8 |

FOREIGN PATENT DOCUMENTS

WO    2012/029855    3/2012

OTHER PUBLICATIONS

Gritli-Linde et al., Expression patterns of the Tmem16 gene family during cephalic development in the mouse, Gene Expression Patterns, 2009, vol. 9, pp. 178-191.*
Picollo A. et al., TMEM16 proteins: Unknown structure and confusing functions, J. Mol. Biol., Jan. 16, 2015, vol. 427, No. 1, pp. 94-105 (NIH-PA Author Manuscript, pp. 1-20).*
International Search Report and Written Opinion issued Jul. 30, 2013 in International (PCT) Application No. PCT/JP2013/061699.
Balasubramanian et al., "Aminophospholipid Asymmetry: A Matter of Life and Death", Annu. Rev. Physiol., vol. 65, 2003, pp. 701-734.
Van Meer et al., "Membrane lipids: where they are and how they behave", Nature Reviews Molecular Cell Biology, vol. 9, Feb. 2008, pp. 112-124.
Nagata et al., "Autoimmunity and the Clearance of Dead Cells", Cell, vol. 140, Mar. 5, 2010, pp. 619-630.
Zwaal et al., "Lipid-protein interactions in blood coagulation", Biochimica et Biophysica Acta, vol. 1376, 1998, pp. 433-453.
Boas et al., "Phosphatidylserine exposure and red cell viability in red cell aging and in hemolytic anemia", Proc. Natl. Acad. Sci. USA, vol. 95, Mar. 1998, pp. 3077-3081.
Yoshida et al., "Phosphatidylserine-dependent engulfment by macrophages of nuclei from erythroid precursor cells", Nature, vol. 437, Sep. 29, 2005, pp. 754-758.
Sessions et al., "Differentiation-related Differences in the Plasma Membrane Phospholipid Asymmetry of Myogenic and Fibrogenic Cells", Biochimica et Biophysica Acta, vol. 728, 1983, p. 103-111.
Helming et al., "Molecular Mediators of macrophage fusion", Trends Cell Biology, vol. 19, No. 10, Sep. 3, 2009, pp. 514-522.
Adler et al., "Monoclonal Antiphosphatidylserine Antibody Inhibits Intercellular Fusion of the Choriocarcinoma Line, JAR", Biology of Reproduction, vol. 53, 1995, pp. 905-910.

(Continued)

*Primary Examiner* — Satyendra K Singh
(74) *Attorney, Agent, or Firm* — Wenderoth, Lind & Ponack, L.L.P.

(57) ABSTRACT

The present invention relates to a method for screening a modulator of a TMEM16 family member, which comprises the following steps:

(1) treating cells expressing the TMEM16 family member with a candidate of the modulator, and
(2) determining whether the candidate alters distribution of a lipid selected from phosphatidylserine, phosphatidylcholine, and galactosylceramide in plasma membrane of the cells, wherein a candidate which increases distribution of phosphatidylserine in the outer leaflet of plasma membrane compared to control is selected as a modulator enhancing a function of the TMEM16 family member, and a candidate which decreases distribution of phosphatidylserine in the outer leaflet of plasma membrane compared to control is selected as a modulator suppressing a function of the TMEM16 family member, and a candidate which increases distribution of phosphatidylcholine or galactosylceramide in the inner leaflet of plasma membrane compared to control is selected as a modulator enhancing a function of the TMEM16 family member, and a candidate which decreases distribution of phosphatidylcholine or galactosylceramide in the inner leaflet of plasma membrane compared to control is selected as a modulator suppressing a function of the TMEM16 family member.

5 Claims, 29 Drawing Sheets

(56) References Cited

OTHER PUBLICATIONS

Gadella et al., "Capacitation Induces Cyclic Adenosine 3',5'-Monophosphate-Dependent, but Apoptosis-Unrelated, Exposure of Aminophospholipids at the Apical Head Plasma Membrane of Boar Sperm Cells", Biology of Reproduction, vol. 67, 2002, pp. 340-350.
Leventis et al., "The Distribution and Function of Phosphatidylserine in Cellular Membranes", Annu. Rev. Biophys., vol. 39, 2010, pp. 407-427.
Folmer et al., "P4 ATPases—Lipid flippases and their role in disease", Biochimica et Biophysica Acta, vol. 1791, Feb. 27, 2009, pp. 628-635.
Oram et al., "ABCA1—mediated transport of cellular cholesterol and phospholipids to HDL apolipoproteins", Lipid Metabolism, vol. 11, 2000, pp. 253-560.
Williamson et al., "Transbilayer Phospholipid Movements in ABCA1-Deficient Cells", PLoS one, Issue 8, Aug. 2007, e729, pp. 1-15.
Bevers et al., "Phospholipid scramblase: An update", FEBS Letters, vol. 584, Mar. 17, 2010, pp. 2724-2730.
Bassè et al., "Membranes and Bioenergetics: Isolation of an Erythrocyte Membrane Protein that Mediates $Ca^{2+}$-dependent Transbilayer Movement of Phospholipid", J. Biol. Chem., vol. 271, 1996, pp. 17205-17210.
Zhou et al., "Membranes and Bioenergetics: Molecular Cloning of Human Plasma Membrane Phospholipid Scramblase: A Protein Mediating Transbilayer Movement of Plasma Membrane Phospholipids", J. Biol. Chem., vol. 272, 1997, pp. 18240-18244.
Zhou et al., "Normal hemostasis but defective hematopoietic response to growth factors in mice deficient in phospholipid scramblase 1", Blood, vol. 99, No. 11, Jun. 1, 2002, pp. 4030-4038.
Sahu et al., "Phospholipid scramblases: An overview", Archives of Biochemistry and Biophysics, vol. 462, Apr. 17, 2007, pp. 103-114.
Suzuki et al., "Calcium-dependent phospholipid scrambling by TMEM16F", Nature, vol. 468, Dec. 9, 2010, pp. 834-840.
Castoldi et al., "Compound heterozygosity for 2 novel *TMEM16F* mutations in a patient with Scott syndrome", BLOOD, vol. 117, No. 16, Apr. 21, 2011, pp. 4399-4400.
Caputo et al., "TMEM16A, A Membrane Protein Associated with Calcium-Dependent Chloride Channel Activity", Science, vol. 322, Oct. 24, 2008, pp. 590-594.
Schroeder et al., "Expression Cloning of TMEM16A as a Calcium-Activated Chloride Channel Subunit", Cell, vol. 134, Sep. 19, 2008, pp. 1019-1029.
Yang et al., "TMEM16A confers receptor-activated calcium-dependent chloride conductance" Nature, vol. 455, Oct. 30, 2008, pp. 1210-1216.
Shiraishi et al., "Increased cytotoxicity of soluble Fas ligand by fusing isoleucine zipper motif", Biochemical and Biophysical Research Communications, vol. 322, Aug. 5, 2004, pp. 197-202.
Morita et al., "Plat-E: an efficient and stable system for transient packaging of retroviruses", Gene Therapy, vol. 7, 2000, pp. 1063-1066.
Kanki et al., "High-efficiency CAG-FLPe Deleter Mice in C57BL/6J Background", Exp. Anim., vol. 55(2), 2006, pp. 137-141.
Imao et al., "Apaf-1- and Caspase-8-independent apoptosis", Cell Death and Differentiation, vol. 20, Nov. 30, 2012, pp. 343-352.
Akagi et al., "Refractory nature of normal human diploid fibroblasts with respect to oncogene-mediated transformation", PNAS, vol. 100, No. 23, Nov. 11, 2003, pp. 13567-13572.
Watson et al., "Effect of IL-7 on the Growth of Fetal Thymocytes in Culture", The Journal of Immunology, vol. 143, No. 4, Aug. 15, 1989, pp. 1215-1222.
Murai et al., "Myeloid-specific transcriptional activation by murine myeloid zinc-finger protein 2", Proc. Natl. Acad. Sci. USA, vol. 95, Mar. 1998, pp. 3461-3466.
Kuba et al., "Evaluation of the limiting acuity of coincidence detection in nucleus laminaris of the chicken", J Physiol, vol. 552, No. 2, Aug. 1, 2003, pp. 611-620.
Ogasawara et al., "Selective Apoptosis of $CD4^+CD8^+$ Thymocytes by the Anti-Fas Antibody", J. Exp. Med., vol. 181, Feb. 1, 1995, pp. 485-491.
Dive et al., "Analysis and discrimination of necrosis and apoptosis (programmed cell death) by multiparameter flow cytometry", Biochimica et Biophysica Acta, vol. 1133, 1992, pp. 275-285.
Galietta, "The TMEM16 Protein Family: A New Class of Chloride Channels?" Biophysical Journal, vol. 97, Dec. 2009, pp. 3047-3053.
Duran et al., "Physiological roles and diseases of TMEM16/anoctamin proteins: are they all chloride channels?" Acta Pharmacologica Sinica, vol. 31, 2011, pp. 685-692.
Rath et al., "Detergent binding explains anomalous SDS-PAGE migration of membrane proteins", PNAS, vol. 106, No. 6, Feb. 10, 2009, pp. 1760-1765.
Segawa et al., "Constitutive exposure of phosphatidylserine on viable cells," PNAS, Nov. 29, 2011, vol. 108, No. 48, pp. 19246-19251.
Williamson et al., "Phospholipid Scramblase Activation Pathways in Lymphocytes", Biochemistry, vol. 40, Jun. 12, 2001, pp. 8065-8072.
Schoenwaelder et al., "Two distinct pathways regulate platelet phosphatidylserine exposure and procoagulant function" BLOOD, vol. 114, No. 3, Jul. 16, 2009, pp. 663-666.
Martins et al., "Anoctamin 6 is an essential component of the outwardly rectifying chloride channel", PNAS, vol. 108, No. 44, Nov. 1, 2011, pp. 18168-18172.
Hampton et al., "Involvement of extracellular calcium in phosphatidylserine exposure during apoptosis", FEBS Letters, vol. 399, 1996, pp. 277-282.
Hartzell et al., "Anoctamin/TMEM16 family members are $Ca^{2+}$-activated $Cl^-$ channels", J Physiol, vol. 587, No. 10, 2009, pp. 2127-2139.
Schreiber et al., "Expression and Function of Epithelial Anoctamins", J. Bioi. Chem., vol. 285, Jan. 7, 2010, pp. 7838-7845.
Duran et al., "ANOs 3-7 in the anoctamin/TMEM16 $Cl^-$ channel family are intracellular proteins", Am J Physiol Cell Physiol, vol. 302, 2012, pp. C482-C493.
Palmgren et al., "P-Type ATPases", Annu. Rev. Biophys., vol. 40, Feb. 22, 2011, pp. 243-266.
Chen et al., "CLC-0 and CFTR: Chloride Channels Evolved From Transporters", Physiol Rev, vol. 88, 2008, pp. 351-387.
Ferrera et al., "Membrane Transport, Structure, Function, and Biogenesis: Regulation of TMEM16A Chloride Channel Properties by Alternative Splicing", J. Bioi. Chem., vol. 284, Oct. 9, 2009, pp. 33360-33368.
Mizuta et al., "Molecular characterization of GDD1/TMEM16E, the gene product responsible for autosomal dominant *Gnathodiaphyseal dysplasia*", Biochemical and Biophysical Research Communications, vol. 357, Mar. 28, 2007, pp. 126-132.
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, vol. 86, Feb. 12, 2010, pp. 213-221.
Tsutsumi et al., "The Novel Gene Encoding a Putative Transmembrane Protein Is Mutated in *Gnathodiaphyseal dysplasia* (GDD)", Am. J. Hum. Genet., vol. 74, Apr. 29, 2004, pp. 1255-1261.
Vermeer et al., "Targeted Next-Generation Sequencing of a 12.5 Mb Homozygous Region Reveals *ANO10* Mutations in Patients with Autosomal-Recessive Cerebellar Ataxia", The American Journal of Human Genetics, vol. 87, Dec. 10, 2010, pp. 813-819.
Eijnde et al., "Transient expression of phosphatidylserine at cell-cell contact areas is required for myotube formation", Journal of Cell Science, vol. 114, 2001, pp. 3631-3642.
Stowell et al., "Galectin-1 Induces Reversible Phosphatidylserine Exposure at the Plasma Membrane", Molecular Biology of the Cell, vol. 20, Mar. 1, 2009, pp. 1408-1418.
Del Buono et al., "Plasma Membrane Lipid Organization and the Adherence of Differentiating Lymphocytes to Macrophages", Journal of Cellular Physiology, vol. 138, 1989, pp. 61-69.

(56) References Cited

OTHER PUBLICATIONS

Fischer et al., "Antigen recognition induces phosphatidylserine exposure on the cell surface of human CD8+ T cells", BLOOD, vol. 108, No. 13, Dec. 15, 2006, pp. 4094-4101.

Ehlen et al., "Inactivation of Anoctamin-6/Tmem16f, a Regulator of Phosphatidylserine Scrambling in Osteoblasts, Leads to Decreased Mineral Deposition in Skeletal Tissues", Journal of Bone and Mineral Research, vol. 28, No. 2, Feb. 2013, pp. 246-259.

Charlesworth et al., "Mutations in ANO3 Cause Dominant Craniocervical Dystonia: Ion Channel Implicated in Pathogenesis", The American Journal of Human Genetics, vol. 91, Dec. 7, 2012, pp. 1041-1050.

Kashyap et al., "Genomewide mRNA profiling of esophageal squamous cell carcinoma for identification of cancer biomarkers", Cancer Biology &Therapy, vol. 8, No. 1, 2009, pp. 36-46.

Das et al., "NGEP, a Prostate-Specific Plasma Membrane Protein that Promotes the Association of LNCaP Cells", Cancer Res, vol. 67, No. 4, Feb. 15, 2007, pp. 1594-1601.

Suzuki et al., "Scrambling of Phospholipids in the cell membrane by TMEM16F", Biochemistry, vol. 83, No. 11, Nov. 2011, pp. 1050-1054, cited in ISR.

Extended European Search Report issued Oct. 5, 2015 in corresponding European Application No. 13777783.5.

Suzuki et al., "Calcium-dependent Phospholipid Scramblase Activity of TMEM16 Protein Family Members", The Journal of Biological Chemistry, vol. 288, No. 19, Mar. 26, 2013, pp. 13305-13316.

\* cited by examiner

```
         10         20         30         40         50         60
  GGCGCGCCGG ATCCGCCACC ATGGTGCACC ACAGCGGCAG CATCCAGAGC TTCAAGCAGC 70         80         90        100        110        120
  AGAAAGGCAT GAACATCAGC AAGAGCGAGA TCACCACCGA GGCCAGCCTG AAGCCCAGCA 130        140        150        160        170        180
  GAAGAAGCCT GCCCTGCCTG GCCCAGAGCT ACGCCCACAG CAAGAGCCTG AGCCAGAGCG 190        200        210        220        230        240
  CCAGCCTGTT CCAGAGCACC GAGAGCGAGA GCCAGGCCCC TACCAGCGTG ACCTTCCTGA 250        260        270        280        290        300
  GCGCCGACAA GCCCGAGCAC GTGACCAGCG AGGAAAGCAG AAAGGACAGC ACCCTGAAGT 310        320        330        340        350        360
  GCAGCTTCGC CGACCTGAGC GACTTCTGTC TGGCCCTGGG CAAGGACAAG GACTACCTGG 370        380        390        400        410        420
  ACGAGAGCGA GCACGCCAAC TACGACAGAA GCAGACTGCT GAACGACTTC GTGACCAAGG 430        440        450        460        470        480
  ACAAGCCCGC CAGCAAGACC AAGCTGAGCA AGAACGACAT GAGCTATATC GCCAGCAGCG 490        500        510        520        530        540
  CCTGCTGTT CAAGGACGGC AAGAAGAGAA TCGACTACAT CCTGGTGTAC CGCAAGACCA 550        560        570        580        590        600
  ACATCCAGTA CGACAAGAGG AACACCTTCG AGAAGAACCT GAGAGCCGAG GGCCTGATGC 610        620        630        640        650        660
  TGGAAAAAGA GCCCGCTATC GCCAACCCCG ACATCATGTT TATCAAGATC CACATCCCCT 670        680        690        700        710        720
  GGGACACCCT GTGCAAATAC GCCGAGAGAC TGAACATCAG GGTGCCCTTC CGGAAGAAGT 730        740        750        760        770        780
  GCTACTACAC CGACCAGAAG AACAAGAGCA AGAGCAGGGT GCAGAACTAC TTCAAGCGGA 790        800        810        820        830        840
  TCAAGAAATG GATGAGCCAG AACCCCATGG TGCTGGACAA GAGCGCCTTC CCCGAGCTGG 850        860        870        880        890        900
  AAGAGAGCGA CTGCTACACC GGCCCCTTCA GCAGAGCCAG AATCCACCAC TTCATCATCA 910        920        930        940        950        960
  ACAACAAGGA CACCTTCTTC AGCAACGCCA CCAGATCCAG AATCGTGTAC CACATGCTGG 970        980        990       1000       1010       1020
  AACGGACTAA GTACGAGAAC GGCATCAGCA AAGTGGGCAT CAGAAAGCTG ATCACCAACG 1030       1040       1050       1060       1070       1080
  GCTCCTATAT CGCCGCCTTC CCACCCCACG AGGGCGCCTA CAAGAGCAGC CTGCCCATCA
```

Fig. 7B

```
         1090       1100       1110       1120       1130       1140
    AGACCCACGG CCCCCAGAAC AACAGACATC TGCTGTACGA GAGATGGGCC AGATGGGGAA 1150       1160       1170       1180       1190       1200
    TGTGGTACAA GCACCAGCCC CTGGACCTGA TCAGAATGTA CTTCGGCGAG AAGATCGGCC 1210       1220       1230       1240       1250       1260
    TGTACTTCGC CTGGCTGGGC TGGTACACCG GCATGCTGAT CCCTGCCGCC GTCGTGGGCC 1270       1280       1290       1300       1310       1320
    TGTGCGTGTT CTTCTACGGC CTGGTCACCA TGAACGAGTC CCAGGTGTCC CAGGAAATCT 1330       1340       1350       1360       1370       1380
    GCAAGGCCAC CGAGGTGTTC ATGTGCCCCC TGTGCGACAA GAACTGCAGC CTGCAGAGGC 1390       1400       1410       1420       1430       1440
    TGAACGACAG CTGCATCTAC GCCAAAGTGA CCTACCTGTT CGACAACGGC GGCACCGTGT 1450       1460       1470       1480       1490       1500
    TCTTCGCCAT CTTCATGGCT ATCTGGGCTA CCGTGTTCCT GGAATTTTGG AAGAGAAGGC 1510       1520       1530       1540       1550       1560
    GGAGCATCCT GACCTACACC TGGGACCTGA TCGAGTGGGA GGAAGAGGAA GAGACACTGA 1570       1580       1590       1600       1610       1620
    GGCCCCAGTT CGAGGCCAAG TACTACAGAA TGGAAGTGAT CAACCCCATC ACCGGCAAGC 1630       1640       1650       1660       1670       1680
    CTGAGCCCCA CCAGCCCAGC AGCGACAAAG TGACCAGACT GCTGGTGTCC GTGTCCGGCA 1690       1700       1710       1720       1730       1740
    TCTTCTTCAT GATCAGCCTG GTCATCACCG CCGTGTTCGC CGTGGTGGTG TACAGACTGG 1750       1760       1770       1780       1790       1800
    TGGTCATGGA ACAGTTCGCC AGCTTCAAGT GGAACTTCGT GAAGCAGCAC TGGCAGTTCG 1810       1820       1830       1840       1850       1860
    CCACCAGCGG AGCCGCCGTG TGCATCAACT TTATCATCAT CATGCTGCTG AACCTGGCCT 1870       1880       1890       1900       1910       1920
    ATGAGAAGAT CGCCTACCTG CTGACCAACC TGGAATACCC CAGAACCGAG TCCGAGTGGG 1930       1940       1950       1960       1970       1980
    AGAACAGCTT CGCCCTGAAG ATGTTCCTGT TCCAGTTCGT GAACCTGAAC AGCTCTATCT 1990       2000       2010       2020       2030       2040
    TCTATATCGC CTTCTTCCTG GGCCGCTTCG TGGGCCACCC CGGCAAGTAC AACAAGCTGT 2050       2060       2070       2080       2090       2100
    TCGAGAGGTG GCGGCTGGAA GAGTGCCACC CCAGCGGCTG CCTGATCGAC CTGTGCCTGC 2110       2120       2130       2140       2150       2160
    AGATGGGCGT GATCATGTTC CTGAAGCAGA TTTGGAACAA CTTCATGGAA CTGGGCTACC
```

Fig. 7C

```
         2170       2180       2190       2200       2210       2220
    CCCTGATCCA GAACTGGTGG TCCAGACACA AGATCAAGAG AGGCATCCAG GACGCCAGCA 2230       2240       2250       2260       2270       2280
    TCCCCCAGTG GGAGAATGAC TGGAACCTGC AGCCCATGAA CATCCACGGC CTGATGGACG 2290       2300       2310       2320       2330       2340
    AGTACCTGGA AATGGTGCTG CAGTTCGGCT TCACCACCAT CTTCGTGGCC GCTTTCCCCC 2350       2360       2370       2380       2390       2400
    TGGCCCCTCT GCTGGCCCTG CTGAACAACA TCATCGAGAT CAGACTGGAC GCCTACAAGT 2410       2420       2430       2440       2450       2460
    TCGTGACCCA GTGGCGGAGG CCCCTGCCTG CCAGAGCCAC AGACATCGGC ATCTGGCTGG 2470       2480       2490       2500       2510       2520
    GCATCCTGGA AGGCATCGGA ATCCTGGCCG TGATCACAAA CGCCTTCGTG ATCGCCATCA 2530       2540       2550       2560       2570       2580
    CCAGCGATTA CATCCCCCGC TTCGTGTACG AGTATAAGTA CGGCCCCTGC GCCAACCACG 2590       2600       2610       2620       2630       2640
    TGAAGCAGAA CGAGAACTGC CTGAAGGGCT ACGTGAACAA CAGCCTGAGC TTCTTCGACC 2650       2660       2670       2680       2690       2700
    TGTCCGAGCT GGGCATGGGC AAGAGCGGCT ACTGCAGATA CAGAGACTAC AGAGGCCCCC 2710       2720       2730       2740       2750       2760
    CTTGGAGCAG CAAGCCCTAC GAGTTCACCC TGCAGTACTG GCACATCCTG GCCGCCAGAC 2770       2780       2790       2800       2810       2820
    TGGCCTTCAT CATCGTGTTC GAGCACCTGG TGTTCGGCAT CAAGTCCTTC ATTGCCTACC 2830       2840       2850       2860       2870       2880
    TGATCCCCGA CATCCCCAAG GGCCTGAGAG AGAGAATCAG ACGCGAGAAG TACCTGGTGC 2890       2900       2910       2920       2930       2940
    AGGAAATGAT GTACGAGGCT GAGCTGGAAC ATCTGCAGCA GCAGAGAAGA AAGAGCGGCC 2950       2960       2970       2980       2990       3000
    AGCCCATCCA CCACGAGTGG CCTGAATTCT TAATTAA
```

Fig. 8A

```
         10         20         30         40         50         60
 GGCGCGCCGG ATCCGCCACC ATGGAAGCCA GCAGCAGCGG CATCACCAAC GGCAAGAACA 70         80         90        100        110        120
 AGGTGTTCCA CGCCGAGGGC GGCCTGGACC TGCAGAGCCA CCAGCTGGAC ATGCAGATCC 130        140        150        160        170        180
 TGCCCGACGG CCCCAAGAGC GACGTGGACT TCAGCGAGAT CCTGAACGCC ATCCAGGAAA 190        200        210        220        230        240
 TGGCCAAGGA CGTCAACATC CTGTTCGACG AGCTGGAAGC CGTGAACAGC CCCTGCAAGG 250        260        270        280        290        300
 ACGACGACAG CCTGCTGCAC CCCGGCAACC TGACCAGCAC CAGCGAGGAC ACCAGCAGAC 310        320        330        340        350        360
 TGGAAGCTGG CGGCGAGACA GTGCGCGAGA GAAACAAGAG CAACGGCCTG TACTTCAGGG 370        380        390        400        410        420
 ACGGCAAGTG CAGAATCGAC TACATCCTGG TGTACAGAAA GAGCAACCCC CAGACCGAGA 430        440        450        460        470        480
 AGAGAGAGGT GTTCGAGAGG AACATCAGAG CCGAGGGCCT GCAGATGGAA AAAGAGAGCA 490        500        510        520        530        540
 GCCTGATCAA CAGCGACATC ATCTTCGTGA AGCTGCACGC CCCCTGGGAG GTGCTGGGCA 550        560        570        580        590        600
 GATACGCCGA GCAGATGAAC GTGCGGATGC CCTTCAGACG GAAAATCTAC TACCTGCCCA 610        620        630        640        650        660
 GGCGGTACAA GTTCATGAGC AGGATCGACA AGCAGATCAG CAGGTTCAGA CGGTGGCTGC 670        680        690        700        710        720
 CCAAGAAACC CATGAGACTG GACAAAGAGA CACTGCCCGA CCTGGAAGAG AACGACTGCT 730        740        750        760        770        780
 ACACCGCCCC CTTCAGCCAG CAGAGAATCC ACCACTTCAT CATCCACAAC AAGGACACAT 790        800        810        820        830        840
 TCTTCAACAA CGCCACCAGA TCCAGGATCG TGCACCACAT CCTGCAGAGG ATTAAGTACG 850        860        870        880        890        900
 AGGAAGGGAA GAACAAGATC GGCCTGAACA GACTGCTGAC CAACGGCAGC TACGAGGCCG 910        920        930        940        950        960
 CCTTCCCACT GCACGAGGGC AGCTACAGAA GCAAGAACAG CATCAAGACC CACGGCGCTG 970        980        990       1000       1010       1020
 TGAACCACAG ACATCTGCTG TACGAGTGCT GGGCCAGCTG GGGCGTGTGG TACAAGTACC 1030       1040       1050       1060       1070       1080
 AGCCCCTGGA CCTCGTGCGG AGATACTTCG GCGAGAAGAT CGGACTGTAC TTCGCCTGGC
```

Fig. 8B

```
         1090       1100       1110       1120       1130       1140
    TGGGCTGGTA CACCGGCATG CTGTTCCCTG CCGCCTTTAT CGGCCTGTTC GTGTTCCTGT 1150       1160       1170       1180       1190       1200
    ACGGCGTGAC CACCCTGGAC CACTGCCAGG TGTCCAAAGA AGTGTGCCAG GCCACCGACA 1210       1220       1230       1240       1250       1260
    TCATCATGTG CCCCGTGTGC GACAAGTACT GCCCCTTCAT GAGACTGAGC GACAGCTGCG 1270       1280       1290       1300       1310       1320
    TGTACGCCAA AGTGACCCAC CTGTTCGACA ACGGCGCCAC CGTGTTCTTC GCCGTGTTCA 1330       1340       1350       1360       1370       1380
    TGGCCGTGTG GGCTACCGTG TTCCTGGAAT TTTGGAAGAG GCGGAGAGCC GTGATCGCCT 1390       1400       1410       1420       1430       1440
    ACGACTGGGA CCTGATCGAC TGGGAGGAAG AAGAGGAAGA GATCCGGCCC CAGTTCGAGG 1450       1460       1470       1480       1490       1500
    CCAAGTACAG CAAGAAAGAA CGGATGAACC CCATCAGCGG CAAGCCCGAG CCCTACCAGG 1510       1520       1530       1540       1550       1560
    CCTTCACCGA CAAGTGCAGC AGACTGATCG TGTCCGCCAG CGGCATCTTC TTCATGATCT 1570       1580       1590       1600       1610       1620
    GCGTCGTGAT CGCCGCCGTG TTCGGCATCG TGATCTACAG AGTGGTCACC GTGTCCACCT 1630       1640       1650       1660       1670       1680
    TCGCCGCCTT CAAGTGGGCC CTGATCAGAA ACAACAGCCA GGTGGCCACC ACCGGCACCG 1690       1700       1710       1720       1730       1740
    CCGTGTGTAT CAACTTCTGC ATCATCATGC TGCTGAACGT CCTGTACGAG AAGGTGGCCC 1750       1760       1770       1780       1790       1800
    TGCTGCTGAC AAAACCTGGAA CAGCCCAGAA CCGAGAGCGA GTGGGAGAAC AGCTTCACCC 1810       1820       1830       1840       1850       1860
    TGAAGATGTT TCTGTTTCAG TTCGTGAACC TGAACAGCTC TACCTTCTAT ATCGCCTTCT 1870       1880       1890       1900       1910       1920
    TCCTGGGACG GTTCACCGGC CACCCTGGCG CCTACCTGAG ACTGATCAAC CGGTGGCGGC 1930       1940       1950       1960       1970       1980
    TGGAAGAGTG CCACCCCAGC GGCTGCCTGA TCGACCTGTG CATGCAGATG GGCATCATTA 1990       2000       2010       2020       2030       2040
    TGGTCCTGAA GCAGACCTGG AACAACTTCA TGGAACTGGG CTACCCCCTG ATCCAGAACT 2050       2060       2070       2080       2090       2100
    GGTGGACCAG ACGGAAAGTG CGGCAGGAAC ACGGCACCGA GAGAAAGATC AACTTCCCCC 2110       2120       2130       2140       2150       2160
    AGTGGGAGAA GGACTACAAC CTGCAGCCCA TGAACGCCTA CGGCCTGTTT GACGAGTACC
```

Fig. 8C

```
        2170       2180       2190       2200       2210       2220
   TGGAAATGAT CCTGCAGTTC GGCTTCACCA CCATCTTCGT GGCCGCTTTC CCCCTGGCCC 2230       2240       2250       2260       2270       2280
   CCCTGCTGGC TCTGCTGAAC AACATCATCG AGATCAGACT GGACGCCTAC AAGTTCGTGA 2290       2300       2310       2320       2330       2340
   CCCAGTGGCG GAGGCCCCTG GCTAGCAGAG CCAAGGACAT CGGCATTTGG TACGGCATCC 2350       2360       2370       2380       2390       2400
   TGGAAGGCAT CGGCATCCTG AGCGTGATCA CCAACGCCTT CGTGATCGCT ATCACCAGCG 2410       2420       2430       2440       2450       2460
   ACTTCATCCC CAGACTGGTG TACGCCTATA AGTACGGCCC CTGTGCTGGC CAGGGCGAGG 2470       2480       2490       2500       2510       2520
   CTGGACAGAA ATGCATGGTC GGATACGTGA ACGCCAGCCT GAGCGTGTTC AGAATCAGCG 2530       2540       2550       2560       2570       2580
   ACTTCGAGAA CAGAAGCGAG CCCGAGAGCG ACGGCAGCGA GTTCAGCGGC ACCCCCCTGA 2590       2600       2610       2620       2630       2640
   AGTACTGCAG ATACAGAGAC TACAGGGACC CCCCCCACAG CCTGGCCCCT TACGGCTACA 2650       2660       2670       2680       2690       2700
   CCCTGCAGTT CTGGCACGTG CTGGCCGCCA GACTGGCCTT CATCATCGTG TTCGAGCACC 2710       2720       2730       2740       2750       2760
   TGGTGTTCTG CATCAAGCAC CTGATCAGCT ACCTGATCCC CGACCTGCCC AAGGACCTGA 2770       2780       2790       2800       2810       2820
   GAGACAGAAT GCGGAGAGAG AAGTACCTGA TTCAGGAAAT GATGTACGAG GCCGAGCTGG 2830       2840       2850       2860       2870       2880
   AAAGACTGCA GAAAGAGCGC AAAGAGCGGA AGAAGAACGG CAAGGCCCAC CACAACGAGT 2890       2900       2910       2920       2930       2940
   GGCCCGAATT CTTAATTAA
```

Fig. 9A

```
            10         20         30         40         50         60
     GGCGCGCCGG ATCCGCCACC ATGGTCGAAC AGGAAGGCCT GACCGCCAAA GAGATCGACT
            70         80         90        100        110        120
     ACGCCTTCCA GCAGAACGAG AACCTGGGCA GCAAAGAGAC AAGCTTCCTG ATCCCCGAGG
           130        140        150        160        170        180
     ACCTGCAGAG CCCCCCTGAG AAGAGATTCA ACCTGTTCCT GAGAAGGCGG CTGATGTTCC
           190        200        210        220        230        240
     AGAGAAGCGA GCACAGCAAG GACAGCGTGT TCTTCAGGGA CGGCATCAGA CAGATCGACT
           250        260        270        280        290        300
     TCGTGCTGAG CTACGTCGAG GATCTGAAGA AGGACGGCGA GCTGAAGGCC GAGAGAAGAA
           310        320        330        340        350        360
     GAGAGTTCGA GCAGAACCTG AGAAAGACCG GCCTGGACCT GGAAACCGAG GACAAGCTGA
           370        380        390        400        410        420
     ACAGCGAGGA CGGCAAGACC TACTTCGTGA AGATCCACGC CCCCTGGGAG GTGCTGGTCA
           430        440        450        460        470        480
     CATACGCTGA AGTGCTGGGC ATCAAGATGC CTATCAAGCT GAGCGACATC CCCAGACCCA
           490        500        510        520        530        540
     AGTACCCCCC CCTGTCCTAC ATGCTGGGCG CCGTGAAGCT GCCCAGCAGC GTGAAGTACC
           550        560        570        580        590        600
     CTACCCCCGA GTACTTCACC GCCCAGTTCA GCAGACACAG ACAGGAACTG TTTCTGATCG
           610        620        630        640        650        660
     AGGACGAGGC CACATTCTTC CCAAGCAGCA CCAGAAACCG GATCGTGTAC TACATCCTGA
           670        680        690        700        710        720
     GCAGATGCCC CTTCGGCGTG GAAGAGGGCA AGAAGAAGAT CGGCATCGAG AGACTGCTCA
           730        740        750        760        770        780
     ACAGCAACAC CTACCTGAGC GCCTACCCCC TGCACGACGG ACAGTACTGG AAGCCCAGCA
           790        800        810        820        830        840
     AGACCACCAG GCCCAACGAG AGGTACAACC TGTGCAAGAA CTGGGCCAGA TTCAGCTACT
           850        860        870        880        890        900
     TCTACAAAGA GCAGCCCTTC CACCTGATCC GGAACTACTT CGGCGAAAAG ATCGGGATCT
           910        920        930        940        950        960
     ACTTTGTGTT CCTGGGCTAC TACACCGAGA TGCTGCTGTT CGCCGCCCTC GTGGGACTGG
           970        980        990       1000       1010       1020
     CCTGCTTCAT CTACGGCCTG CTGAGCATGG AAAACAACAG AACCAGCACC GAAATCTGCG
          1030       1040       1050       1060       1070       1080
     ACCCCGACAT CGGCGGCCAG ATGATCATGT GCCCCCTGTG CGACGAAGTG TGCGACTACT
```

Fig. 9B

```
          1090       1100       1110       1120       1130       1140
     GGCGGCTGAA CACCACCTGT CTGCACTCCA AGTTCAGCCA CCTGTTCGAT AACGAGAGCA 1150       1160       1170       1180       1190       1200
     CAGTGTTCTT CGCCCTGTTC ATGGGAATCT GGGTCACCCT GTTCCTCGAA TTTTGGAAGC 1210       1220       1230       1240       1250       1260
     AGAGACAGGC CAGACTGGAA TACGAGTGGG ACCTGGTGGA CTTCGAGGAA GAACAGCAGC 1270       1280       1290       1300       1310       1320
     AGCTGCAGCT CAGACCCGAG TTCGAGGCCA TGTGCAAGCA CAAGAAAATG AACCCCGTGA 1330       1340       1350       1360       1370       1380
     CCAAAGAAAT GGAACCCCAC ATGCCCCTGT GCCACAGAAT CCCTTGGTAC TTCGTGTCCG 1390       1400       1410       1420       1430       1440
     GCACCACCGT GACCTTCGGC ATGGCTCTGC TGCTGAGTAG CATGGTGTCC ATCCTGATCT 1450       1460       1470       1480       1490       1500
     ACAGACTGAG CGTGTTCGCC ACCTTCGCCA GCTTCATGGA AAGCGAGGCC ACCCTGCAGT 1510       1520       1530       1540       1550       1560
     CCGTGAAGAG TTTCTTCACA CCCCAGCTGG CCACCGCCCT GAGCGGCTCT TGCCTGAACT 1570       1580       1590       1600       1610       1620
     GCATCGTGAT CCTGATCCTC AACTTCTTCT ACGAGAAGAT CAGCGCCTGG ATCACCAAGA 1630       1640       1650       1660       1670       1680
     TGGAAATCCC TAGAACCCAC CAGGAATATG AGAGCAGCCT GACCCTGAAG ATGTTCCTGT 1690       1700       1710       1720       1730       1740
     TCCAGTTCGT GAACTACTAC AGCTCCTGCT TCTACGTGGC CTTCTTCAAG GGCAAGTTCG 1750       1760       1770       1780       1790       1800
     TGGGCTACCC CGGCAGCTAC ACCTACATGT TCAACATCTG GCGGAGCGAG GAATGCGGCC 1810       1820       1830       1840       1850       1860
     CTGCCGGCTG TCTGATCGAA CTGACCACCC AGCTGACCAT CATCATGATC GGCAAGCAGA 1870       1880       1890       1900       1910       1920
     TTTTCGGCAA CATCCACGAG GCTTTCCAGC CCCTGATCTT TAACTGGTGG CGCAGAAGAA 1930       1940       1950       1960       1970       1980
     GGGCCAGAAC CCACAGCGAG AAGCTGTACT CCAGATGGGA GCAGGACCAC GACCTCCAGG 1990       2000       2010       2020       2030       2040
     TGTACGGCCA CAGAGGCCTG TTCTACGAGT ATCTGGAAAC AGTGATCCAG TTCGGCTTCG 2050       2060       2070       2080       2090       2100
     CCACACTGTT CGTGGCTAGC TTCCCCCTGG CCCCTCTGTT CGCCCTGATG AACAACATCA 2110       2120       2130       2140       2150       2160
     TGGGCATCAG AGTGGACGCC TGGAAGCTGA CCACACAGTA CAGACGGCCC GTGGCCGCCA
```

Fig. 9C

```
          2170       2180       2190       2200       2210       2220
     AGGCTCACTC TATTGGCGTG TGGCAGGACA TCCTGTTTGG CATGGCCATC GTGTCCGTGG 2230       2240       2250       2260       2270       2280
     CCACCAACGC CTTCATCGTG TCTTTCACCA GCGACATCAT CCCCAGGCTG GTGTACTTCT 2290       2300       2310       2320       2330       2340
     ACGCCTACAG CACCAACAGC ACCGAGCCCC TGTCCGGCTA CGTGAACAAC AGCCTGTCCG 2350       2360       2370       2380       2390       2400
     TGTTCCTGAT CGCTGACTTC CCCAACCACA CCGTGCCCAT GGAAAAGAAA GACTTCGTGA 2410       2420       2430       2440       2450       2460
     CCTGCCGGTA CAGGGACTAC AGATACCCCC CCGACCACGA GGATAAGTAC AGCCACAACA 2470       2480       2490       2500       2510       2520
     TGCAGTTTTG GCACGTGCTG GCCGCTAAGA TGACCTTCAT CATCGTGATG GAACACGTGG 2530       2540       2550       2560       2570       2580
     TGTTTCTGTT CAAGTTCCTG CTGGCCTGGC TGATCCCTGA CGTGCCCAAG GACGTGGTGG 2590       2600       2610       2620       2630       2640
     AAAAGATCAA GAGGGAAAAG CTGATGACCA TCAAGATCAT CCACGATTTC GAGCTGAACA 2650       2660       2670       2680       2690       2700
     AGCTCAAAGA GAATCTGGAC GTCGAGTACG GGAACATCAT GAAGAACGTG CTGGTGGACG 2710       2720       2730       2740       2750       2760
     AGGACAACTC CCTGAAGGCC AAGACCACAG TGGAATTCTT AATTAA
```

METHOD FOR SCREENING A MODULATOR OF A TMEM16 FAMILY MEMBER

This application claims priority to and the benefit of the U.S. Provisional Application No. 61/624,491, filed on Apr. 16, 2012, the entire content of which is incorporated herein by reference.

TECHNICAL FIELD

The present invention relates to a method for screening a modulator of a TMEM16 family member.

BACKGROUND ART

Phospholipids and glycosphingolipids are distributed asymmetrically in plasma membrane leaflets, with phosphatidylserine (PS) and phosphatidylethanolamine (PE) in the inner leaflet, and phosphatidylcholine (PC), galactosylceramide (GalCer) and glucosylceramide (GluCer) mainly in the outer leaflet (1,2). The lipid asymmetry is disrupted in various processes, including apoptotic cell death (3), activated platelets (4), red blood cell aging (5), pyrenocyte formation in definitive erythropoiesis (6), fusion of macrophages, myocytes, or cytotrophoblasts (7-9), and sperm capacitation (10).

Distribution of lipids in plasma membranes is regulated by three types of lipid transporters: flippases, floppases and scramblases. Flippases, also called ATP-dependent aminophospholipid translocases, transport aminophospholipids from the extracellular leaflet to the cytoplasmic side (1,11). The type IV-P-type ATPases (P4-ATPase), a subfamily of the P-type ATPase multispan transmembrane proteins, are strong candidates for flippases (12). Floppases are transporters that move a wide range of lipids from the cytosolic to the extracellular leaflet in an ATP-dependent manner. The ATP-binding cassette (ABC) ATPase, particularly ABCA1, has been proposed as a floppase (13), but ABCA1-deficient cells exhibit no defects in transbilayer phospholipid movement (14) arguing against this role.

Once established, the phospholipid distribution between the outer and inner leaflets is not easily disrupted; ATP-dependent translocase inactivation alone does not appear sufficient to cause the rapid PS exposure seen in apoptotic cell death and platelet activation. Thus, a phospholipid scramblase that bi-directionally and non-specifically transports phospholipids in response to Ca2+ has been proposed (15). Using a liposome reconstitution system with synthetic phospholipids, Basse et al. (16) purified a 37-kDa protein from human erythrocytes, and named it phospholipid scramblase (PLSCR). Its cDNA was then isolated (17). However, since the $Ca^{2+}$-induced PS exposure is normal in PLSCR1$^{-/-}$ cells (18), PLSCR's function as a phospholipid scramblase has been challenged (15,19).

By repeatedly selecting cell populations that efficiently exposed PS in response to $Ca^{2+}$ ionophore, we recently established a subline of mouse pro B cell line (Ba/F3) that constitutively exposes PS (20). The Ba/F3 subline harbours a mutated form of TMEM16F protein, a protein carrying eight transmembrane regions with cytoplasmic N- and C-termini. Ba/F3 cells carrying the mutated form of TMEM16F constitutively exposed PS and PE, and internalized PC and SM. We thus proposed TMEM16F as a phospholipid scramblase (20). Confirming that TMEM16F is a Ca2+-dependent phospholipid scramblase, recessive TMEM16F mutations were identified in human patients with Scott syndrome (20,21), which is known to result from a phospholipid-scrambling defect; these patients suffer from impaired blood clotting. However, it is not clear if TMEM16F is involved in other processes, such as apoptotic cell death or cell fusion. Two of the TMEM16 family's 10 members, TMEM16A and 16B, are $Ca^{2+}$-dependent Cl$^-$ channels (22-24); this raises a question of whether TMEM16F is likewise a Cl$^-$ channel, and whether any other TMEM16 family members are phospholipid scramblases.

SUMMARY OF INVENTION

We established an immortalized fetal thymocyte (IFET) cell line from fetal thymus of mice carrying a floxed TMEM16F allele. IFETs express TMEM16F, 16H, and 16K, and expose PS in response to a $Ca^{2+}$ ionophore. Deleting TMEM16F in the IFETs completely abolished their ability to expose PS in response to $Ca^{2+}$-ionophore. On the other hand, Fas ligand (FasL) treatment efficiently induced PS exposure in the TMEM16F− deficient cells. In the presence of TMEM16C, 16D, 16F, 16G, and 16J, TMEM16F$^{-/-}$ IFETs responded to $Ca^{2+}$ ionophore by scrambling phospholipids and galactosylceramide, while other family members did not. On the other hands, the two family members, TMEM16A and 16B, but not others showed the $Ca^{2+}$-dependent Cl$^-$ channel activity. Based on those results, the present invention is archived.

The present invention provides:
1. A method for screening a modulator of a TMEM16 family member, which comprises the following steps:
   (1) treating cells expressing the TMEM16 family member with a candidate of the modulator, and
   (2) determining whether the candidate alters distribution of a lipid selected from phosphatidylserine, phosphatidylcholine, and galactosylceramide in plasma membrane of the cells,
   wherein a candidate which increases distribution of phosphatidylserine in the outer leaflet of plasma membrane compared to control is selected as a modulator enhancing a function of the TMEM16 family member, and a candidate which decreases distribution of phosphatidylserine in the outer leaflet of plasma membrane compared to control is selected as a modulator suppressing a function of the TMEM16 family member, and
   a candidate which increases distribution of phosphatidylcholine or galactosylceramide in the inner leaflet of plasma membrane compared to control is selected as a modulator enhancing a function of the TMEM16 family member, and a candidate which decreases distribution of phosphatidylcholine or galactosylceramide in the inner leaflet of plasma membrane compared to control is selected as a modulator suppressing a function of the TMEM16 family member;
2. The method of 1 above, wherein the TMEM16 family member is TMEM 16C and the lipid is selected from phosphatidylcholine and galactosylceramide;
3. The method of 1 above, wherein the TMEM16 family member is TMEM 16D and the lipid is selected from phosphatidylserine, phosphatidylcholine, and galactosylceramide;
4. The method of 1 above, wherein the TMEM16 family member is TMEM 16G and the lipid is selected from phosphatidylserine, phosphatidylcholine, and galactosylceramide; and
5. The method of 1 above, wherein the TMEM16 family member is TMEM 16J and the lipid is selected from phosphatidylserine, phosphatidylcholine, and galactosylceramide.

In another embodiment, the present invention provides the followings:
6. A method for screening a modulator of a TMEM16 family member, which comprises the following steps:
   (1) treating cells expressing the TMEM16 family member with a candidate of the modulator, and
   (2) determining whether the candidate alters distribution of a lipid selected from phosphatidylserine and phosphatidylcholine in plasma membrane of the cells,
wherein a candidate which increases distribution of phosphatidylserine in the outer leaflet of plasma membrane compared to control is selected as a modulator enhancing a function of the TMEM16 family member, and a candidate which decreases distribution of phosphatidylserine in the outer leaflet of plasma membrane compared to control is selected as a modulator suppressing a function of the TMEM16 family member, and
a candidate which increases distribution of phosphatidylcholine in the inner leaflet of plasma membrane compared to control is selected as a modulator enhancing a function of the TMEM16 family member, and a candidate which decreases distribution of phosphatidylcholine in the inner leaflet of plasma membrane compared to control is selected as a modulator suppressing a function of the TMEM16 family member;
7. The method of 6 above, wherein the TMEM16 family member is TMEM 16C and the lipid is phosphatidylcholine;
8. The method of 6 above, wherein the TMEM16 family member is TMEM 16D and the lipid is selected from phosphatidylserine and phosphatidylcholine;
9. The method of 6 above, wherein the TMEM16 family member is TMEM 16G and the lipid is phosphatidylcholine; and
10. The method of 6 above, wherein the TMEM16 family member is TMEM 16J and the lipid is phosphatidylcholine.

Figure 1A:
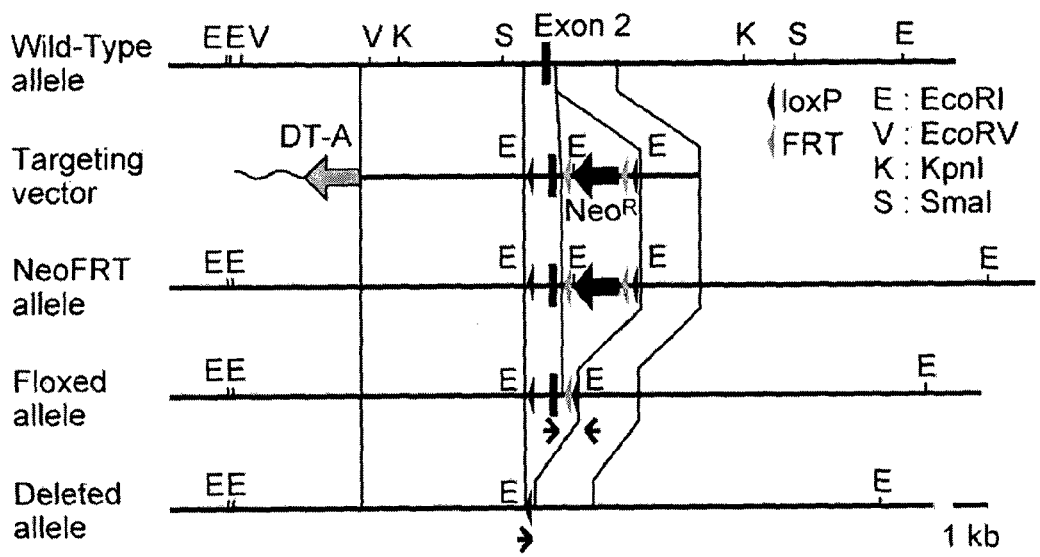
FIG. 1A-1D: Establishment of TMEM16F$^{-/-}$ IFET Cell Line.
Figure 1B:
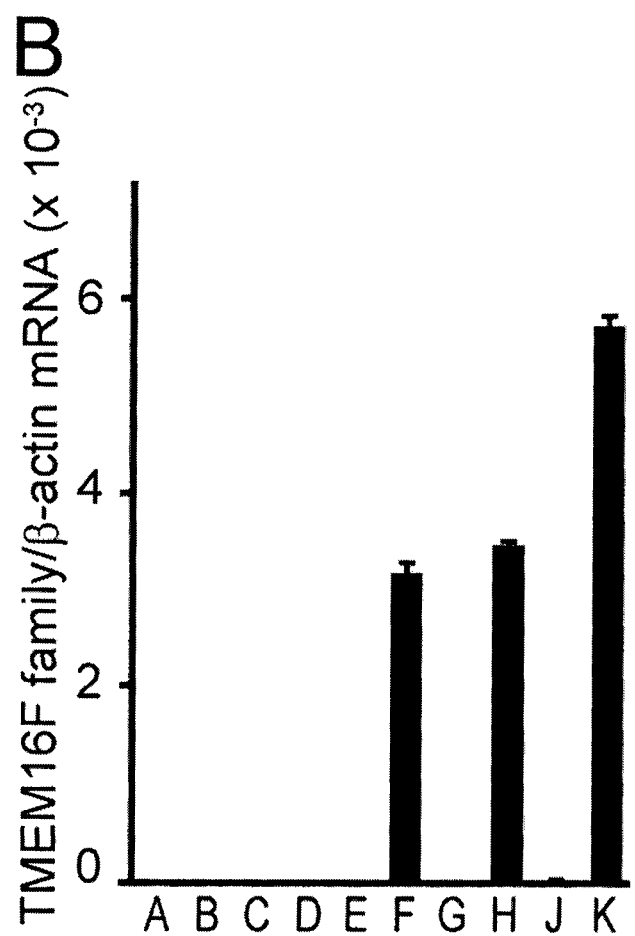
Figure 1C:
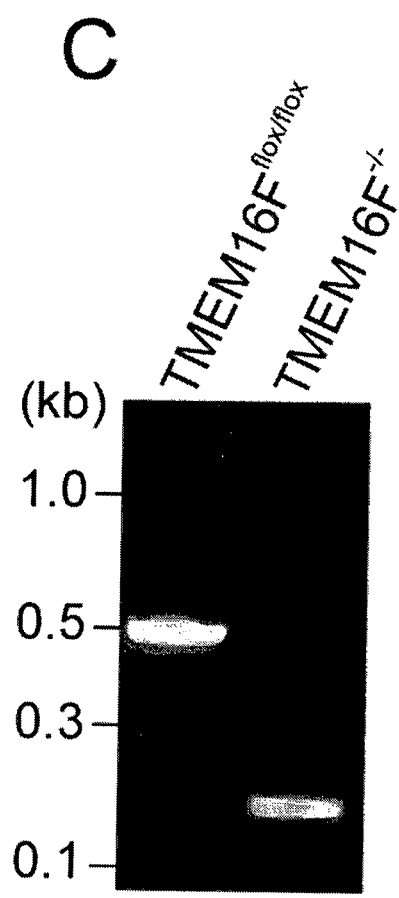

A, Schematic representation of wild-type and mutant TMEM16F alleles together with the targeting vector. Recognition sites for Eco RI (E), Eco RV (V), Kpn I (K), and Sma I (S) in the flanking region of exon 2 (filled box) are indicated. In the target vector, a 1.0-kb DNA fragment carrying exon 2 and its flanking region was replaced by a 2.7-kb fragment carrying two loxP sequences (filled arrowhead) and PGK-neo (Neo$^R$) flanked by FRT sequences (gray arrowhead). Diphtheria toxin A-fragment (DT-A) driven by the tk promoter was inserted at 5' site of the vector. In NeoFRT allele, TMEM16F chromosomal gene was replaced by the targeting vector. In Floxed allele, the FRT-flanked NeoR gene was removed by FLPe recombinase. In deleted allele, the loxP-flanked exon 2 of TMEM16F gene was deleted by Cre recombinase. Primers used in FIG. 1C are indicated by arrows. Scale bar, 1.0 kb.

B, Real-time PCR analysis for mRNA of TMEM16F family members in IFETs. An IFET cell line was established from TMEM16F$^{flox/flox}$ fetal thymocytes. TMEM16A-16H, 16J and 16K mRNA in TMEM16F$^{flox/flox}$ IFETs was quantified by real-time PCR, and expressed relative to β-actin mRNA. The experiment was carried out for three times, and the average value was plotted with S.D. (bar).

C, Deletion of TMEM16F exon 2 in the IFET cell line. TMEM16F$^{flox/flox}$ IFETs were infected by Cre-bearing adenovirus to establish TMEM16F$^{-/-}$ IFET cells. Chromosomal DNA from TMEM16F$^{flox/flox}$ and TMEM16F$^{-/-}$ IFETs was analyzed by PCR with the primers indicated in FIG. 1A.

D, Western blots for TMEM16F in TMEM16F$^{flox/flox}$ and TMEM16F$^{-/-}$ IFETs. Cell lysates (10 μg proteins) were separated by 7.5% SDS-PAGE, and blotted with rabbit anti-TMEM16F serum (upper panel) or anti-α-tubulin antibody (lower panel). Molecular weight standards (Precision Plus Standard, Bio-Rad) are shown in kDa at left.

FIG. 2A-2G: An Indispensable Role of TMEM16F for Ca$^{2+}$-Induced but not Apoptotic PS Exposure.

A, Ca$^{2+}$ ionophore induced PS exposure. TMEM-16F$^{flox/flox}$ and TMEM16F$^{-/-}$ IFETs were treated at 20° C. with 3.0 μM A23187 in the presence of Cy5-labeled Annexin V. Annexin V-binding to the cells was monitored by flow cytometry for 10 min, and expressed in MFI (mean fluorescence intensity).

B and C, Ca$^{2+}$ ionophore induced lipid internalization. TMEM16F$^{flox/flox}$ and TMEM16F$^{-/-}$ IFETs were treated at 15° C. with 250 nM A23187 in the presence of 100 nM NBD-PC (B) or 250 nM NBD-GalCer (C). Using aliquots of the reaction mixture, the BSA-non extractable level of NBD-PC or NBD-GalCer in the SytoxBlue-negative population was determined at the indicated time by FACSAria, and expressed in MFI.

D, Transformation of IFETs with mouse Fas. TMEM16F$^{flox/flox}$ and TMEM16F$^{-/-}$ IFETs were infected with a retrovirus carrying mouse Fas, and were stained with a PE-labeled hamster mAb against mouse Fas. The staining profile of parental cells is also shown.

E-G, FasL-induced apoptosis. Fas-expressing TMEM16F$^{flox/flox}$ and TMEM16F$^{-/-}$ IFETs were treated at 37° C. for 2 h with 60 units/ml FasL in the absence or presence of 50 μM Q-VD-OPh. In E, the cells were permeabilized with 90% methanol, and stained with rabbit anti-active caspase 3 followed by incubation with Alexa 488-labeled goat anti-rabbit IgG. In F, cells were stained with Cy5-labeled Annexin V and PI and analyzed by FACSAria. In G, cells were analyzed by FACSAria before and after FasL treatment; the FSC and SSC profiles are shown.

Figure 3A:
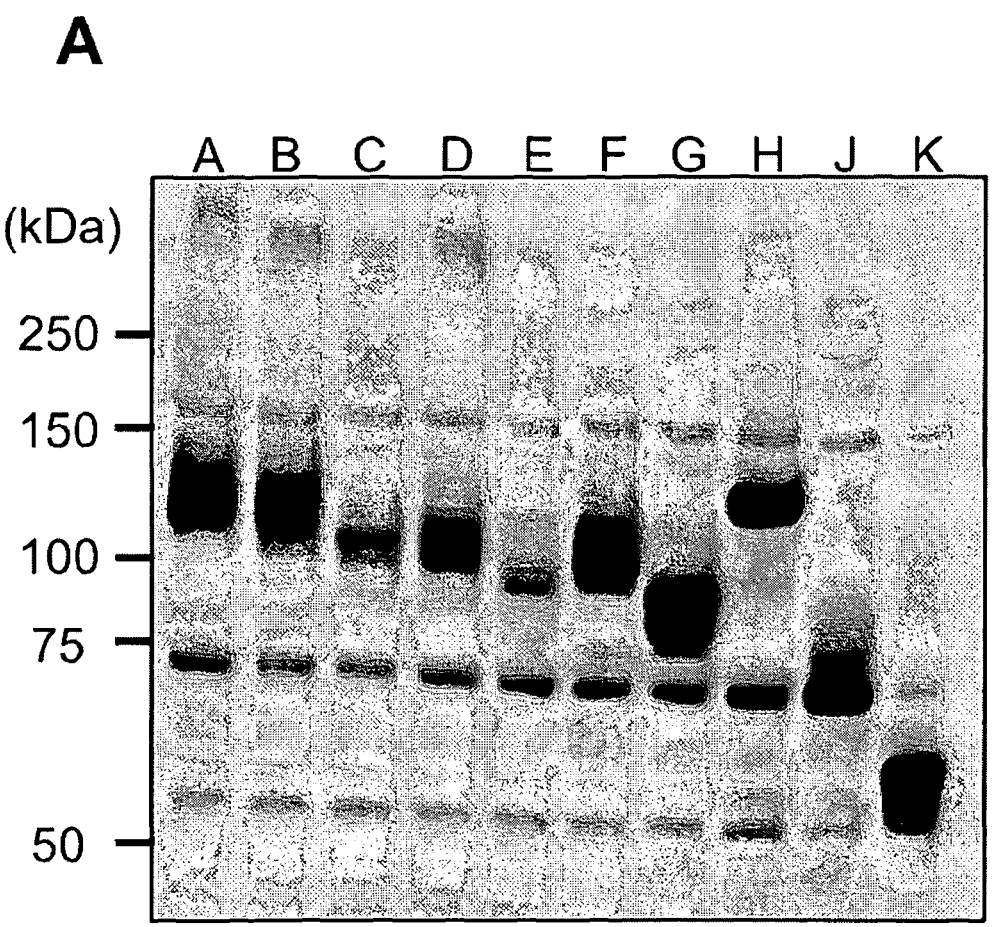
Figure 3B:
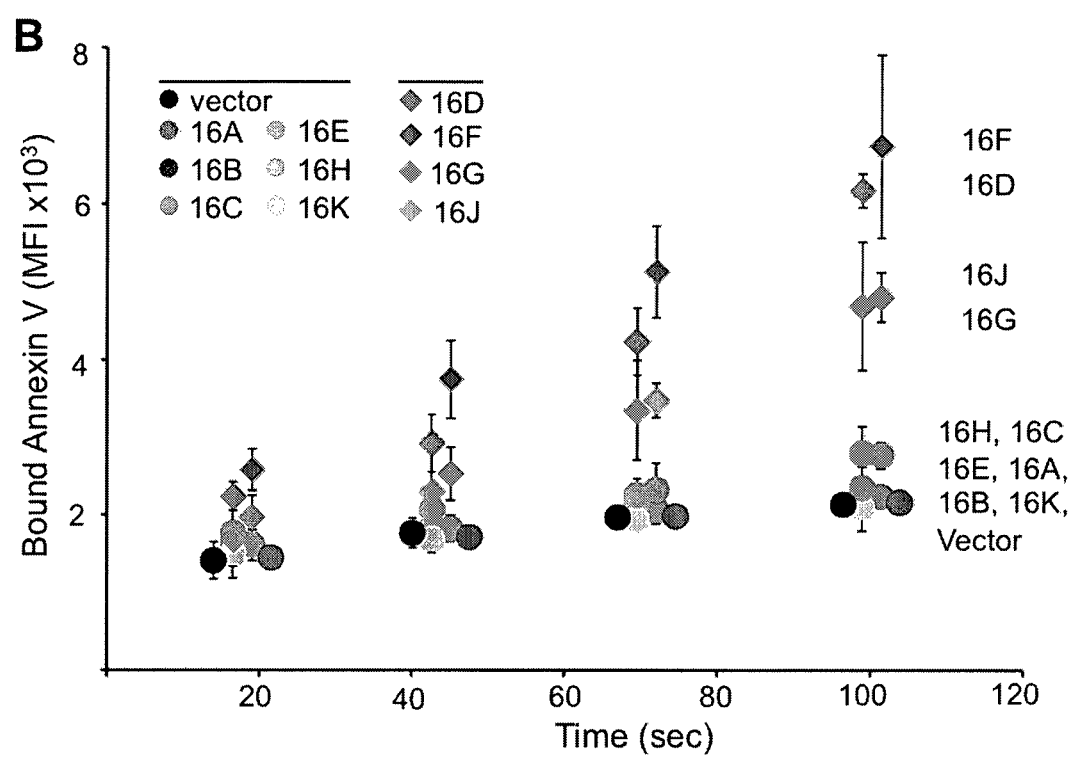

FIG. 3A-3B: Ca$^{2+}$-Dependent PS Exposure by TMEM16 Family Members.

The ten TMEM16 family members were FLAG-tagged at C-terminus and introduced into TMEM16F$^{-/-}$ IFETs to establish stable transformants.

A, Western blotting. TMEM16 protein expression in each transformant was analyzed by Western blotting with an anti-FLAG mAb. Note that the amount of TMEM16K lysate protein analyzed was one-eighth that of the others.

B, Ca$^{2+}$-induced PS exposure by TMEM16 family members. TMEM16F$^{-/-}$ IFETs transformed with the indicated TMEM16 family member were stimulated with 3.0 μM A23187. Annexin V binding was monitored with a FACSAria at 20° C. for 2 min, and expressed in MFI. The experiments were carried out for three times, and the average values were plotted with S.D. (bars).

Figure 4A:
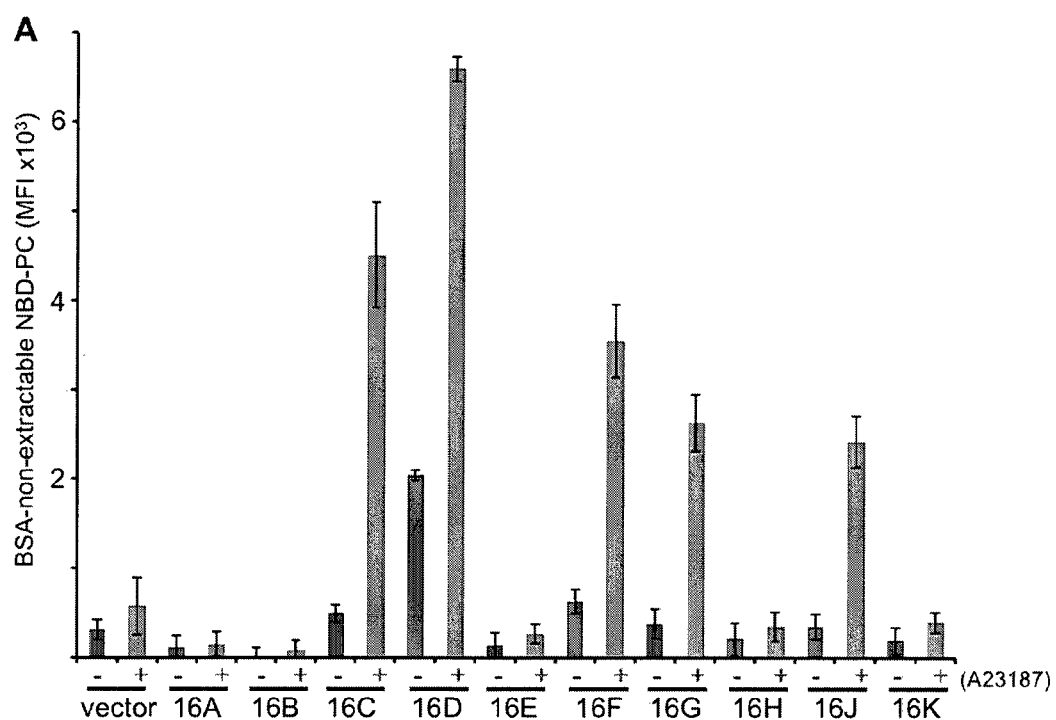
Figure 4B:
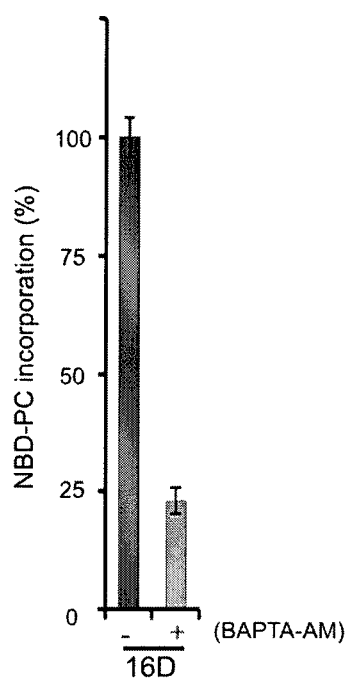
Figure 4C:
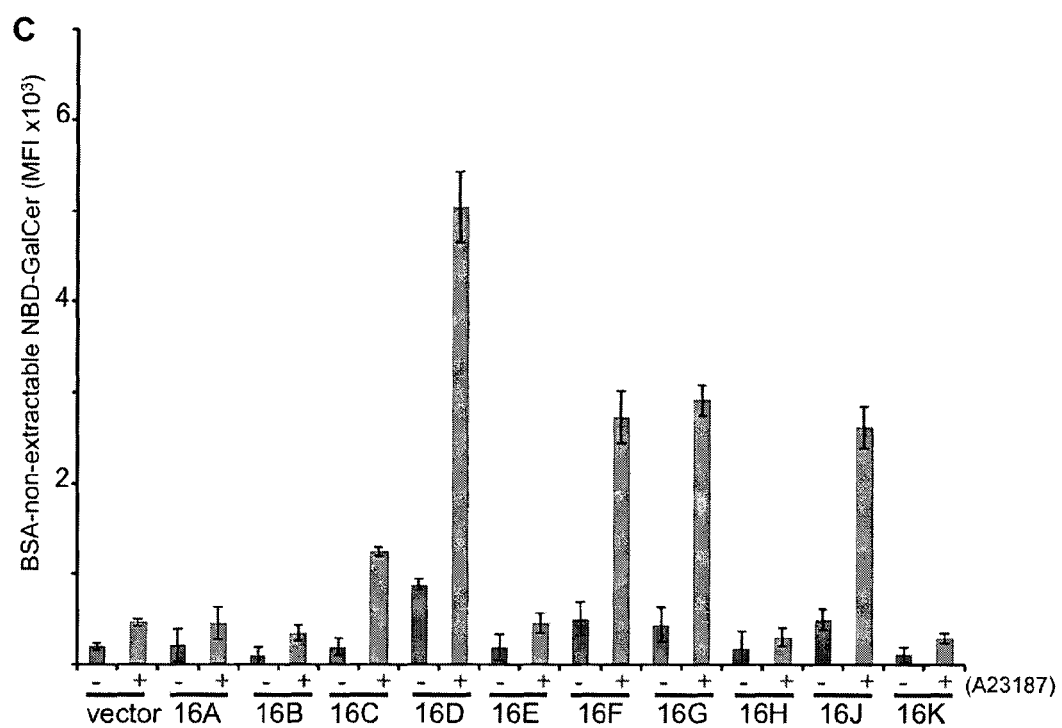

FIG. 4A-4C: Ca$^{2+}$-Dependent Internalization of NBD-PC and NBD-GalCer by TMEM16 Family Members.

A and C, The ability of TMEM16 family members to internalize NBD-PC and NBD-GalCer. TMEM16F$^{-/-}$ IFETs transformed with the indicated TMEM16 family member were treated at 15° C. with (+) or without (−) 250 nM A23187 in the presence of 100 nM NBD-PC for 4 min (A) or 250 nM NBD-GalCer for 5 min (C), and the internalized, or BSA-non extractable NBD-PC or NBD-GelCer, was quantified by FACSAria, and expressed in MFI.

B, Requirement of $Ca^{2+}$ for the constitutive internalization of NBD-PC by TMEM16D. The TMEM16D transformants of TMEM16F$^{-/-}$ IFETs were treated with 40 μM BAPTA-AM for 30 min in $Ca^{2+}$-free RPMI, and incubated at 15° C. for 8 min in HBSS containing 1 mM $CaCl_2$ and 100 nM NBD-PC. The internalized NBD-PC was determined as above, and expressed as percentage of the internalized NBD-PC obtained without BAPTA-AM treatment.

All experiments in FIGS. 4A, 4B, and 4C were carried out for three times, and the average values were plotted with S.D. (bars).

Figure 5A:
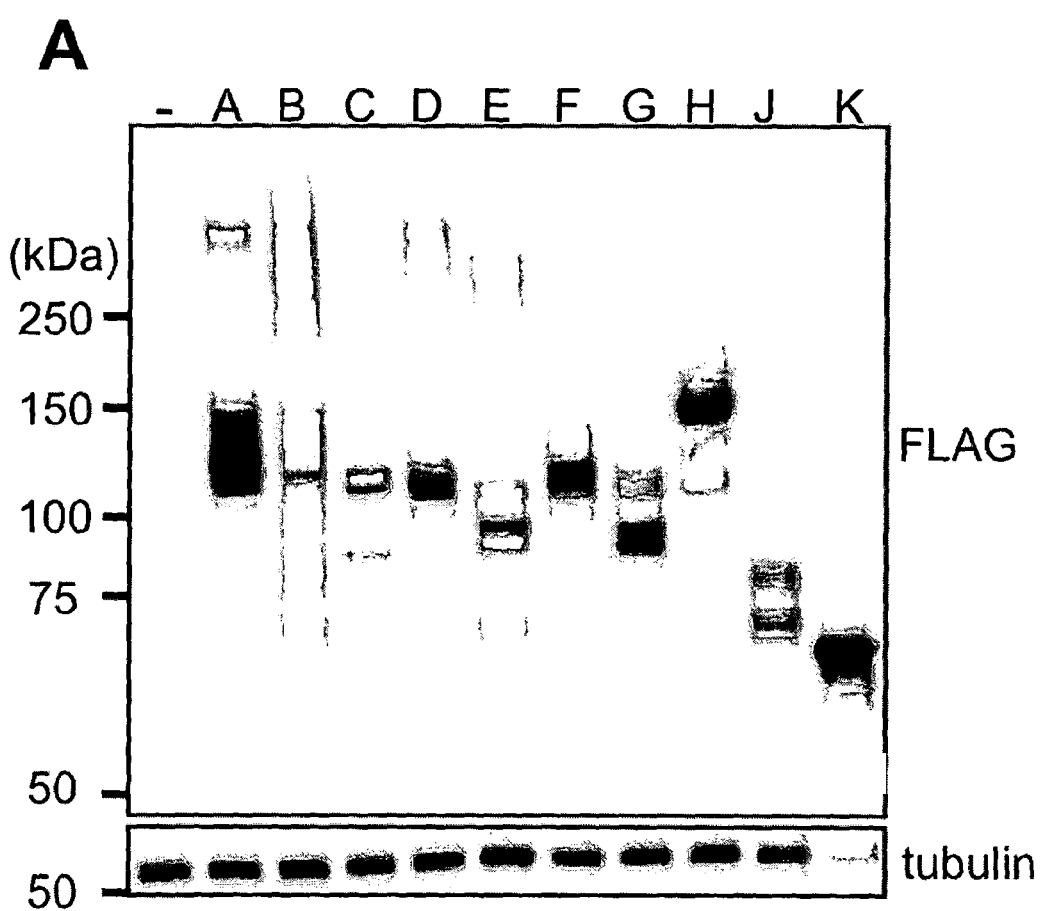
Figure 5B:
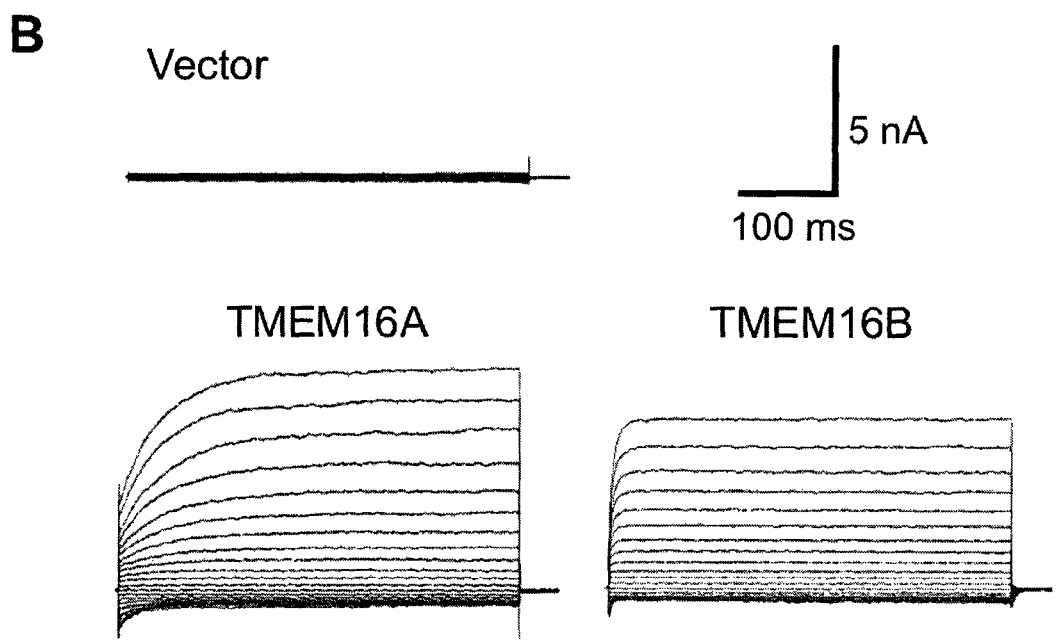
Figure 5C:
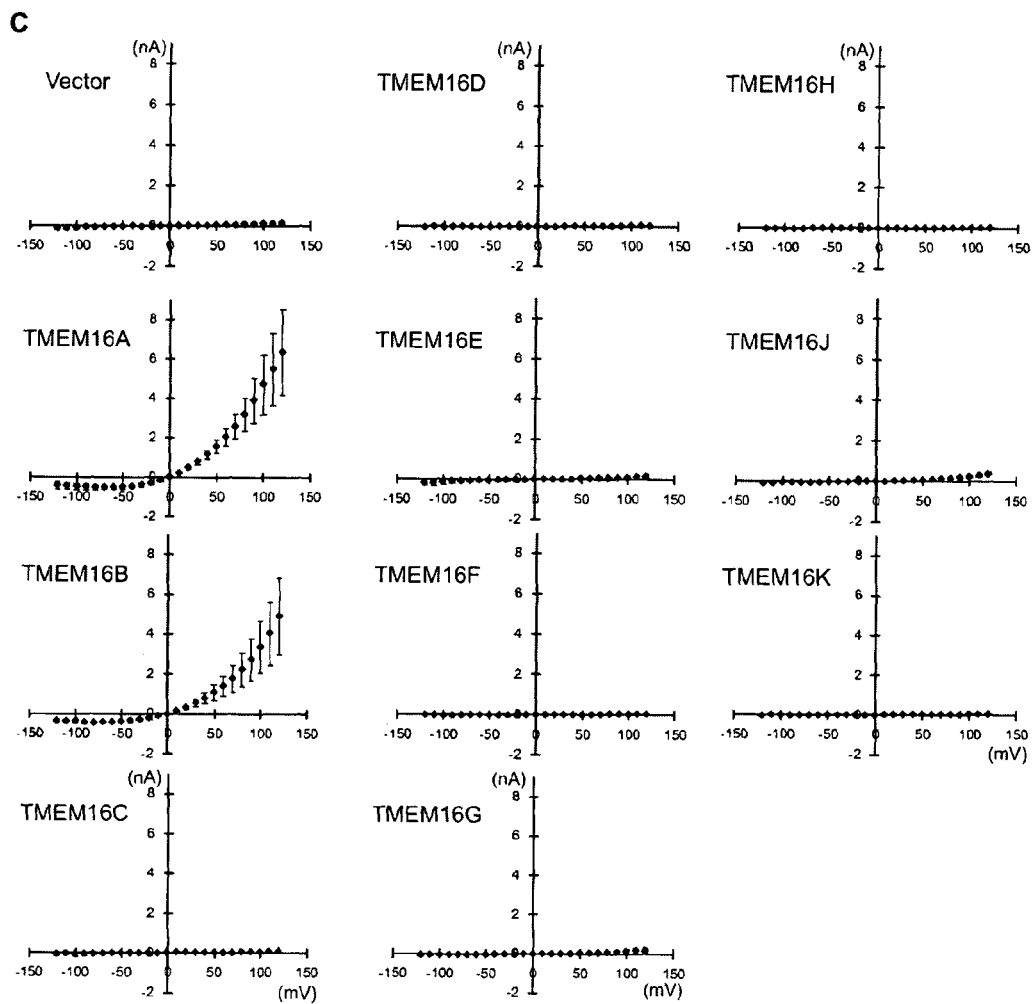

FIG. 5A-5C: $Ca^{2+}$-Dependent $Cl^-$-Channel Activity of TMEM16 Family Members.

A, Expression of TMEM16 family members in HEK293T cells. HEK293T cells were transfected with a pEF-BOS-EX vector carrying cDNA for the flag-tagged TMEM16 family member. Two days later, the expression level of each TMEM16 member was analyzed by Western blotting with anti-Flag and anti-α-tubulin mAbs. Note that the amount of TMEM16K lysate protein analyzed was one-eighth that of the others.

B, $Ca^{2+}$ ionophore-induced TMEM16A and 16B $Cl^-$-channel activity. HEK293T cells were co-transfected with a pEF-BOS-EX vector carrying TMEM16A or 16B cDNA, and pMAX-EGFP. Two days later, the $Cl^-$-channel activity of EGFP-positive cells was examined by electrophysiology. The pipette (intracellular) solution contained 500 nM free $Ca^{2+}$. Representative whole-cell membrane currents elicited at −120 to +120 mV in 10 mV-steps are shown for vector-, TMEM16A-, and 16B-transfected cells. The holding membrane potential was maintained at 0 mV.

C, Outward rectification of the $Cl^-$ current by TMEM16 family members. HEK293T cells were co-transfected with pMAX-EGFP and pEF-BOS-EX vector for the indicated TMEM16 family member, and electrophysiology was carried out as described above. Membrane currents were measured at the indicated voltage pulses (Vm). Experiments were independently done 3-5 times, and the average values were plotted against the applied membrane potential with S.D. (bars).

Figure 6A:
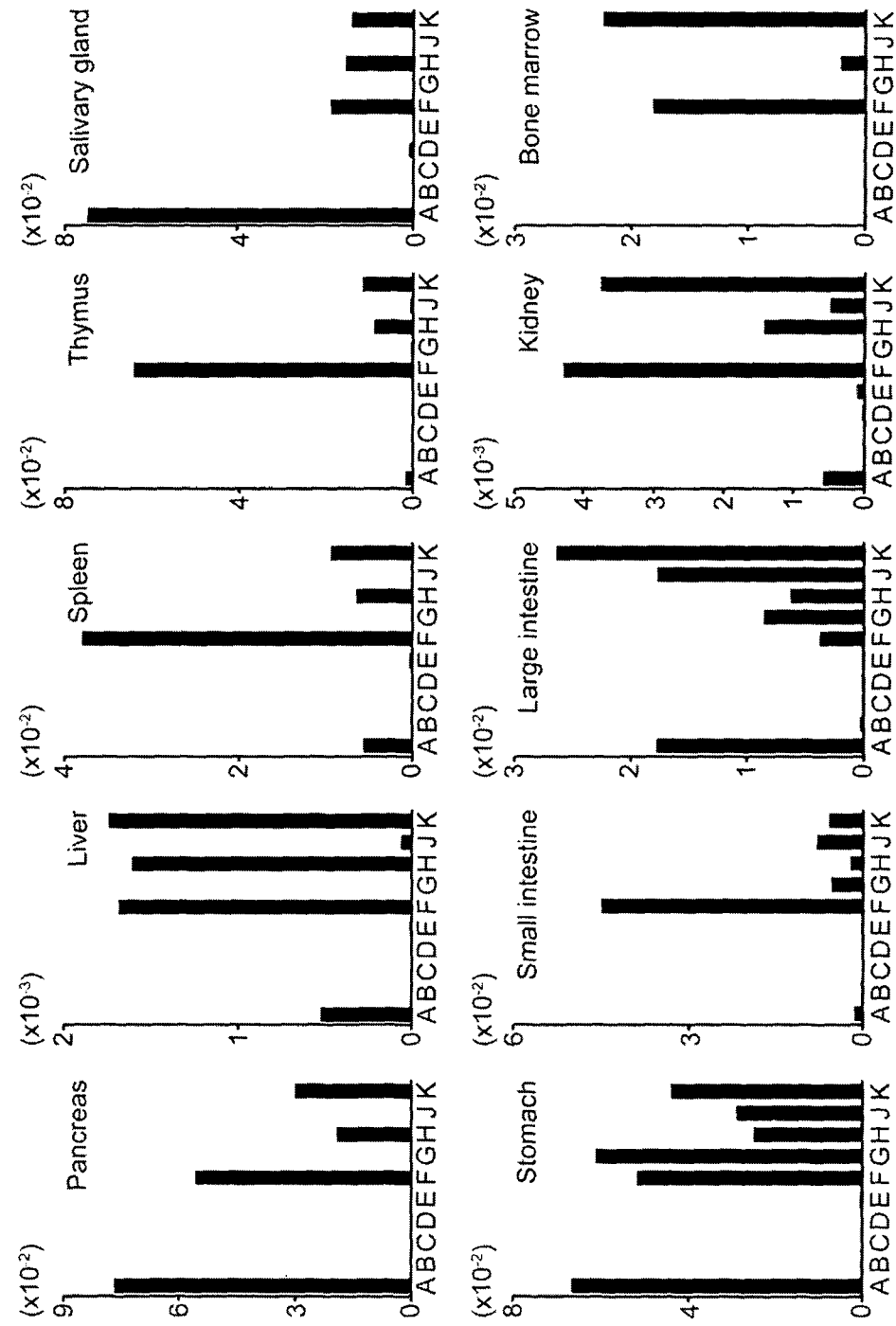
Figure 6B:
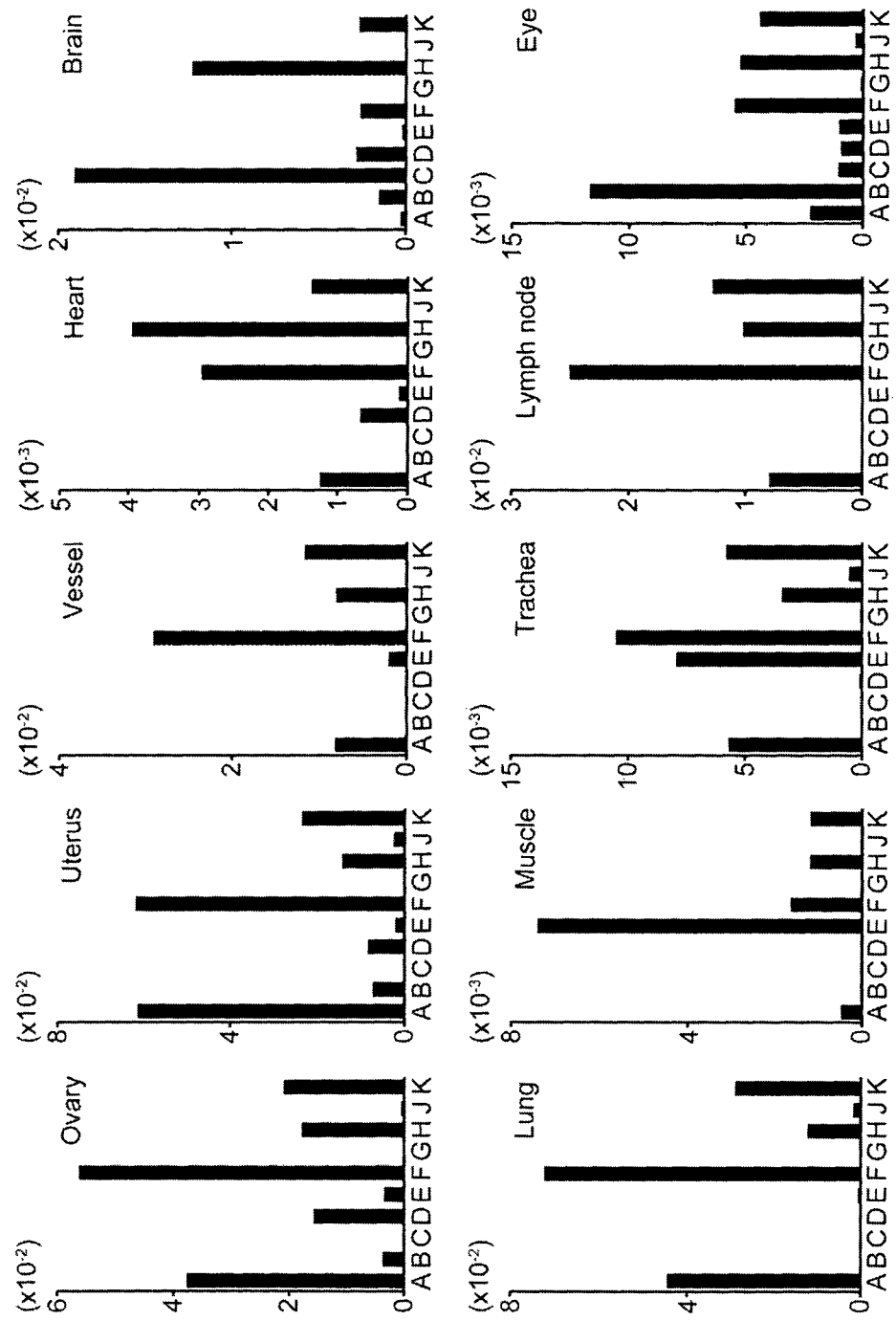
Figure 6C:
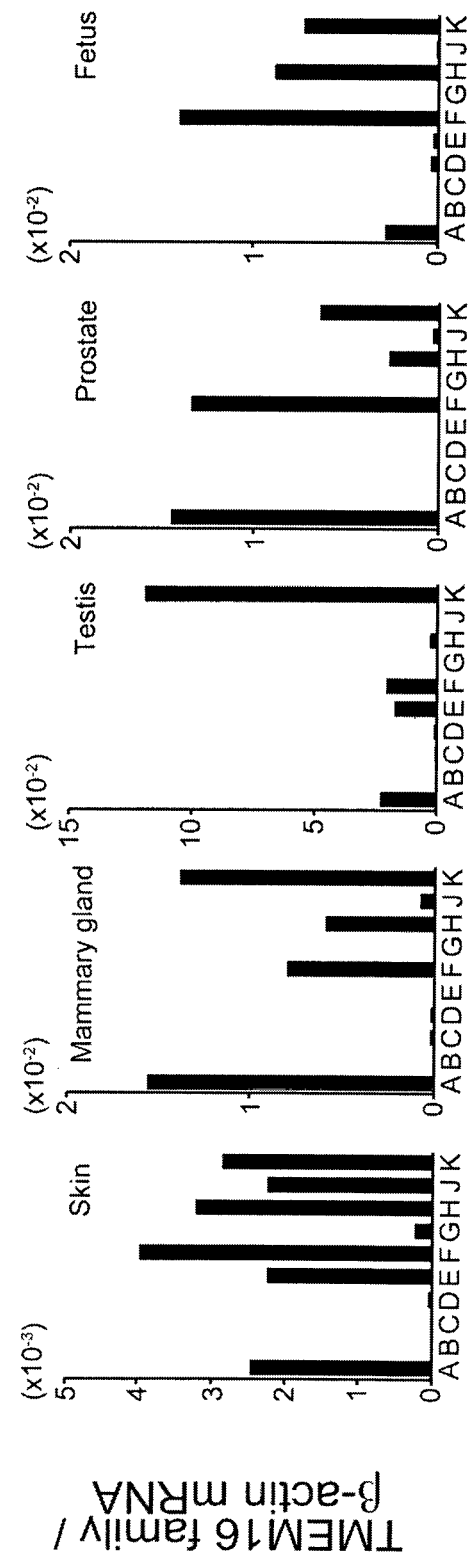

FIG. 6A-6C: Real-Time PCR Analysis for TMEM16 Family Member mRNA in Mouse Tissues.

RNA was prepared from the indicated mouse tissues, and mRNA level quantified by real-time PCR were expressed relative to β-actin mRNA for each TMEM16 family member.

FIG. 7A-7C: The Designed Nucleotide Sequence for Mouse TMEM16C.

The first 20 nucleotides carry Bam H1 (GGATCC) and Kozak sequence for ribosome-binding (CCACC) in front of ATG initiation codon. The coding sequence is followed by an Eco R1 recognition sequence (GAATTC).

FIG. 8A-8C: The Designed Nucleotide Sequence for Mouse TMEM16D.

The first 20 nucleotides carry Bam H1 (GGATCC) and Kozak sequence for ribosome-binding (CCACC) in front of ATG initiation codon. The coding sequence is followed by an Eco R1 recognition sequence (GAATTC).

FIG. 9A-9C: The Designed Nucleotide Sequence for Mouse TMEM16E.

The first 20 nucleotides carry Bam H1 (GGATCC) and Kozak sequence for ribosome-binding (CCACC) in front of ATG initiation codon. The coding sequence is followed by an Eco R1 recognition sequence (GAATTC).

DESCRIPTION OF EMBODIMENTS

"A TMEM16 family member" is a protein which has 8 transmembrane regions with cytosolic N- and C-termini. Although ten TMEM16 family members are known (35, 36), "a TMEM16 family member" in the present invention is selected from TMEM16C, TMEM16D, TMEM16G, and TMEM16J. The TMEM16 family member of the present invention may be derived from, but not limited to, human, monkey, mice, or rabbit. The amino acid sequences of human TMEM16C, TMEM16D, TMEM16G, and TMEM16J are disclosed under the NCBI reference number NP_113606.2 (TMEM16C), NP_849148.2 (TMEM16D), NP_001001666.1 (TMEM16G), and NP_001012302.2 (TMEM16J).

"A candidate of a modulator of a TMEM16 family member may be a natural or synthetic product, and may be low-molecular compounds, proteins, nucleic acid molecules, peptides, antibodies, or cell extract or culture supernatant of microorganisms, plants or animals. The candidate may be provided in a form of a library, such as a library of low-molecular compounds, peptides, or antibodies.

As used herein, "cells expressing a TMEM16 family member" includes cells which express the TMEM16 family member in nature from the genome, and cells which express the TMEM16 family member from a gene encoding the TMEM16 family member which has been introduced into the cells. The cells may be derived from, but not limited to, human, monkey, mice, or rabbit. For example, human HeLa, human EBV (Epstein Barr Virus)-transformed B cell line, mouse MEF (embryonal fibroblasts), and mouse pro B cell line Ba/F3 may be used in the present invention.

"A modulator of a TMEM16 family member" includes both "a modulator enhancing a function of a TMEM16 family member" and "a modulator suppressing a function of a TMEM16 family member". As used herein, "enhancing (or suppressing) a function of a TMEM16 family member" means promoting (or inhibiting) a biological function of a TMEM16 family member as a lipid scramblase in cells or animals. "A modulator of a TMEM16 family member" may be an agent directly affecting the function of the TMEM16 family member protein, or an agent increasing or decreasing expression of the TMEM16 family member. "Increasing or decreasing expression of a TMEM16 family member" includes increasing or decreasing mRNA expression from a gene encoding the TMEM16 family member, and increasing or decreasing protein expression of the TMEM16 family member. Therefore, "a modulator of a TMEM16 family member" includes an agent affecting a regulatory sequence of a gene encoding the TMEM16 family member such as a promoter or enhancer, and also includes an antisense oligonucleotide (DNA or RNA), siRNA, miRNA, and lybozyme prepared according to the sequence of the gene encoding the TMEM16 family member.

In the method of the present invention, the enzymatic activity of a TMEM16 family member as a lipid scramblase is measured. The lipid is selected from the group consisting of phosphatidylserine (PS), phosphatidylcholine (PC), and galactosylceramide (GalCer). Under the normal condition, PS is distributed in the inner leaflet of plasma membrane and PC and GalCer are distributed in the outer leaflet of plasma membrane. The TMEM16 family member of the present invention moves PS to the outer leaflet of plasma membrane (i.e., exposes PS) and moves PC and GalCer to the inner leaflet of plasma membrane (i.e., internalizes PC and GalCer). The enzymatic activity of a TMEM16 family member may be measured by determining distribution of the lipid in plasma membrane.

A candidate which increases distribution of phosphatidylserine in the outer leaflet of plasma membrane compared to control is selected as a modulator enhancing a function of the TMEM16 family member, and a candidate which decreases distribution of phosphatidylserine in the outer leaflet of plasma membrane compared to control is selected as a modulator suppressing a function of the TMEM16 family member. A candidate which increases distribution of phosphatidylcholine or galactosylceramide in the inner leaflet of plasma membrane compared to control is selected as a modulator enhancing a function of the TMEM16 family member, and a candidate which decreases distribution of phosphatidylcholine or galactosylceramide in the inner leaflet of plasma membrane compared to control is selected as a modulator suppressing a function of the TMEM16 family member. As used herein, "control" means distribution of the same lipid in the same leaflet in cells expressing the same TMEM16 family member in the absence of the candidate of the modulator.

TMEM16C functions as a scramblase for PC and GalCer. Accordingly, a candidate which increases distribution of PC or GalCer in the inner leaflet of plasma membrane compared to control is selected as a modulator which enhancing a function of TMEM16C, and a candidate which decreases distribution of PC or GalCer in the inner leaflet of plasma membrane compared to control is selected as a modulator suppressing a function of TMEM16C.

TMEM16D functions as a scramblase for PS, PC, and GalCer. Accordingly, a candidate which increases distribution of PS in the outer leaflet of plasma membrane compared to control is selected as a modulator enhancing a function of TMEM16D, and a candidate which decreases distribution of PS in the outer leaflet of plasma membrane compared to control is selected as a modulator suppressing a function of TMEM16D. Also, a candidate which increases distribution of PC or GalCer in the inner leaflet of plasma membrane compared to control is selected as a modulator which enhancing a function of TMEM16D, and a candidate which decreases distribution of PC or GalCer in the inner leaflet of plasma membrane compared to control is selected as a modulator suppressing a function of TMEM16D.

TMEM16G functions as a scramblase for PS, PC, and GalCer. Accordingly, a candidate which increases distribution of PS in the outer leaflet of plasma membrane compared to control is selected as a modulator enhancing a function of TMEM16G, and a candidate which decreases distribution of PS in the outer leaflet of plasma membrane compared to control is selected as a modulator suppressing a function of TMEM16G. Also, a candidate which increases distribution of PC or GalCer in the inner leaflet of plasma membrane compared to control is selected as a modulator which enhancing a function of TMEM16G, and a candidate which decreases distribution of PC or GalCer in the inner leaflet of plasma membrane compared to control is selected as a modulator suppressing a function of TMEM16G.

TMEM16J functions as a scramblase for PS, PC, and GalCer. Accordingly, a candidate which increases distribution of PS in the outer leaflet of plasma membrane compared to control is selected as a modulator enhancing a function of TMEM16J, and a candidate which decreases distribution of PS in the outer leaflet of plasma membrane compared to control is selected as a modulator suppressing a function of TMEM16J. Also, a candidate which increases distribution of PC or GalCer in the inner leaflet of plasma membrane compared to control is selected as a modulator which enhancing a function of TMEM16J, and a candidate which decreases distribution of PC or GalCer in the inner leaflet of plasma membrane compared to control is selected as a modulator suppressing a function of TMEM16J.

In the step "(1) treating cells expressing the TMEM16 family member with a candidate of the modulator", typically, the candidate is added to the culture medium of the cells in the presence of $Ca^{2+}$. When appropriate, calcium ionophore such as A23187 may be added to the culture medium at the same time or after the addition of the candidate.

Distribution of PS in plasma membrane may be determined by detecting the binding between PS exposed to the cell surface and an agent which has a property to bind to PS, such as AnnexinV or MFG-E8 (also called as lactadherin). For example, cells expressing a TMEM16 family member which has been treated with a candidate are treated with fluorescently-labelled AnnexinV and the amount of AnnexinV bound to the cell surface is measured.

Distribution of PS in plasma membrane also may be determined based on blood-clotting reaction. For example, cells expressing a TMEM16 family member are treated with a candidate of the modulator and also with calcium ionophore concurrently with or after the treatment with the candidate, and mixed with agents required for blood coagulation such as factor Xa, factor Va, and prothrombin, and then production of thrombin is measured. Alternatively, fibrinogen may be further added to the cell culture to measure production of fibrin.

Distribution of PC and GalCer in plasma membrane may be determined by using a fluorescently-labeled lipid. As a fluorescent label, NBD and TopFluor may be used. For example, a fluorescently-labeled lipid is added to the culture medium such that the fluorescently-labeled lipid is incorporated into outer leaflet of plasma membrane of cells expressing a TMEM16 family member. When the TMEM16 family member functions as a lipid scramblase, the fluorescently-labeled lipid is moved to the inner leaflet of plasma membrane (i.e., internalized). Therefore, cells expressing a TMEM16 family member may be treated with a candidate of the modulator, and also with calcium ionophore if needed, in the presence of a fluorescently-labeled lipid such as NBD-PC or NBD-GalCer. The cells were then treated with BSA to remove unincorporated NBD-PC or NBD-GalCer, followed by measuring the NBD-PC or NBD-GalCer incorporated into cell by a flow cytometry.

Abnormality (mutations and over-expression) in TMEM16 family members is known to cause various human diseases (36). For example, genetic mutations in TMEM16C, 16E, 16F and 16K are associated with craniocervical dystonia (58), musculoskeletal disorder (49, 51), bleeding disorder (20), and ataxia (52), respectively. TMEM16A and 16G are over-expressed in human gastrointestinal stromal tumors/head and neck squamous carcinoma, and prostate cancer, respectively (59, 60). Therefore, the method of the present invention is useful for the development of therapeutic or prophylactic agents for such diseases.

Example

Experimental Procedures

Materials and Cell Lines

Leucine-zipper-tagged human FasL was produced in COS7 cells as described (25). One unit of FasL is defined as the activity that kills $1.0 \times 10^5$ mouse WR19L cell expressing Fas (W3) cells) in 4 h. A caspase inhibitor, Q-VD-OPh (quinolyl-valyl-O— methylaspartyl-[-2,6-difluorophenoxy]-methyl ketone) was purchased from R&D systems (Minneapolis, Minn.). IFETs were maintained in RPMI medium containing 10% FCS (Nichirei Bioscience, Tokyo, Japan) and 50 μM β-mercaptoethanol. HEK293T and Plat-E cells (26) were cultured in DMEM containing 10% FCS.

cDNA Cloning

Mouse TMEM16F cDNA (NCBI: NM_175344) was described (20). Mouse cDNAs for TMEM16A (GenBank: BC062959.1), 16B (GenBank: BC033409.1), and 16G (GenBank: BC116706.1) were from DNAFORM (Yokohama, Japan). Mouse cDNAs for TMEM16C (NCBI: NM_001128103.1), 16D (Ensemble: ENSMUST00000070175), and 16K (NCBI: NM_133979.2) were cloned from brain tissue by RT-PCR, while cDNAs for TMEM16E (NCBI: NM_177694.5), 16H (NCBI: NM_001164679.1), and 16J (NCBI: NM_178381.3) were isolated from the skeletal muscle, thymus, and stomach, respectively. All cDNAs were verified by sequencing. The following primers were used to isolate TMEM16 cDNAs (the extra sequence for the restriction enzyme is underlined):

```
                                          (SEQ ID NO: 1)
TMEM16A, 5'-ATATGGATCCACCATGAGGGTCCCCGAGAAGTA,
and
                                          (SEQ ID NO: 2)
5'-ATATGAATTCCAGCGCGTCCCCATGGTACT;

TMEM16B,
                                          (SEQ ID NO: 3)
5'-ATATGAATTCCGCATGCACTTTCACGACAACCA,
and
                                          (SEQ ID NO: 4)
5'-ATATGAATTCTACATTGGTGTGCTGGGACC;

TMEM16C,
                                          (SEQ ID NO: 5)
5'-ATATGGATCCAAAATGGTCCACCACTCAGGCTC,
and
                                          (SEQ ID NO: 6)
5'-ATATCAATTGAGGCCATTCATGGTGAATAG;

TMEM16D,
                                          (SEQ ID NO: 7)
5'-ATATAGATCTAAAATGGAGGCCAGCTCTTCTGG,
and
                                          (SEQ ID NO: 8)
5'-ATATCAATTGTGGCCACTCATTGTGATGTG;

TMEM16E,
                                          (SEQ ID NO: 9)
5'-ATATGGATCCGAGATGGTGGAGCAGGAAGGCTT,
and
                                         (SEQ ID NO: 10)
5'-ATATCAATTGGACTGTAGTTTTAGCCTTCA;

TMEM16G,
                                         (SEQ ID NO: 11)
5'-ATATAGATCTGACATGCTGCGGGGGCAAGCGCG,
and
                                         (SEQ ID NO: 12)
5'-ATATGAATTCGCCTCCGGTAACCCCTACTG;

TMEM16H,
                                         (SEQ ID NO: 13)
5'-ATATAGATCTGCCATGGCCGAGGCGGCTTCGGG,
and
                                         (SEQ ID NO: 14)
5'-ATATGAATTCAGGCCTGTGACCTGCGTCCT;

TMEM16J,
                                         (SEQ ID NO: 15)
5'-ATATGAATTCAGCATGCAGGATGATGAGAGTTC,
and
                                         (SEQ ID NO: 16)
5'-ATATCAATTGTACATCCGTGCTCCTGGAAC;

TMEM16K,
                                         (SEQ ID NO: 17)
5'-ATATGGATCCAAGATGAGAGTGACTTTATCAAC,
and
                                         (SEQ ID NO: 18)
5'-ATATCAATTGGGTAGCTTCCTTCCCATCTT.
```

Since the native mouse cDNAs for TMEM16C, 16D, and 16E produced a low level of proteins in mammalian cells, sequences with enhanced mRNA stability and translational efficiency were custom ordered from GENEART (Regensburg, Germany) (FIGS. 7-9, SEQ ID NOS: 19-21).

Establishment of TMEM16F$^{-/-}$ IFET Cell Line

TMEM16F conditionally targeted mice were generated by UNITECH (Chiba, Japan) as a custom order. In brief, a neo-loxP cassette carrying the PGK promoter-driven neo gene and flanked by FRT sequences was inserted into intron 3 of the TMEM16F gene (FIG. 1A). A 1.0 kb-DNA fragment containing exon 2 was replaced with a fragment carrying the corresponding sequence and a loxP sequence. The diphtheria toxin A-fragment (DT-A) driven by the thymidine kinase (tk) promoter, was inserted at 5' end of the vector. Mouse Bruce-4 ES cells were transfected with the targeting vector by electroporation, and G418-resistant clones were screened for homologous recombination by PCR. Positive clones were injected into blastocysts to generate TMEM16F$^{+/NeoFRT}$ mice.

The TMEM16F$^{+/NeoFRT}$ mice were crossed with CAG-FLPe transgenic mice to remove the Neo cassette (27). Offspring were backcrossed to wild-type C57BL/6 mice to remove the CAG-FLPe transgene, generating TMEM16F$^{+/flox}$ mice. Mice were housed in a specific pathogen-free facility at Kyoto University, and all animal experiments were carried out in accordance with protocols approved by Kyoto University.

IFET cell lines were established as described (28). In brief, TMEM16F$^{+/flox}$ mice were intercrossed, and fetal thymocytes were obtained at embryonic day 14.5. Thymocytes were cultured in DMEM containing 10% FCS, 1× non-essential amino acids, 10 mM Hepes-NaOH buffer (pH 7.4), and 50 µM β-mercaptoethanol. Retroviruses carrying genes for H-ras$^{V12}$ and c-myc were produced in Plat-E cells with pCX4 vector (29), concentrated by centrifugation, and attached to RetroNectin-coated plates (Takara Bio, Kyoto, Japan). Thymocytes were attached to the retrovirus-coated plate by centrifugation at 400×g for 5 min, and cultured in medium containing 5 ng/ml mouse IL-7 (PeproTech, Rocky Hill, N.J.) (30). The resultant IFETs were infected with 1×10$^5$ pfu/ml Adeno-Cre (Takara Bio) and cloned by limited dilution. Clones carrying the TMEM16F$^{-/-}$ allele were selected by PCR with following primers: wild-type specific sense primer, CTCCAGAGTTTGTAAGTAACACAT (SEQ ID NO: 22), mutant specific sense primer, CAGTCATCGATGAATTCATAACTT (SEQ ID NO: 23), and common anti-sense primer, AAGACTGATTTCCAAGG TTATCGAA (SEQ ID NO: 24).

Transformation of TMEM16F$^{-/-}$ IFETs

Mouse TMEM16 cDNAs were inserted into pMXs puro c-FLAG (20) to express proteins tagged with FLAG at the C-terminus. Retrovirus was produced in Plat-E cells, and used to infect TMEM16F$^{-/-}$ IFETs. Stable transformants were selected in medium containing 2 µg/ml puromycin. Mouse Fas cDNA (GenBank: NM_007987) was introduced into IFETs by retrovirus-mediated transformation, and its expression was confirmed by flow cytometry with an anti-Fas mAb (Jo2) (MBL, Nagoya, Japan).

Real-Time PCR

Total RNA was reverse-transcribed using Superscript III reverse-transcriptase (Invitrogen, Carlsbad, Calif.) or a High Capacity RNA-to-cDNA™ kit (Applied Biosystems, Foster City, Calif.). Aliquots of the products were amplified in a reaction mixture containing LightCycler®480 SYBR Green I Master (Roche Diagnostics, Basel, Switzerland). Primers used for real-time PCR were as follows: TMEM16A, 5'-AC- CCCGACGCCGAATGCAAG (SEQ ID NO: 25), and 5'-GCTGGTCCTGCCTGACGCTG (SEQ ID NO: 26); 16B, 5'-GAGGCGCACACCTGGGTCAC (SEQ ID NO: 27), and 5'-ATGGGGCGTGGATCCGGACA (SEQ ID NO: 28); 16C, 5'-GCCAGCAATTGCCAACCCCG (SEQ ID NO: 29), and 5'-GCAGTCCGACTCCTCCAGCTCT (SEQ ID NO: 30); 16D, 5'-ACAGGCATGCTCTTCCCCGC (SEQ ID NO: 31), and 5'-GCGATCACTGCTCGGCGTCT (SEQ ID NO: 32); 16E, 5'-AGCAGCTCCAGCTTCGGCCT (SEQ ID NO: 33), and 5'-TTCACGCTCTGCAGGGTGGC (SEQ ID NO: 34); 16F, 5'-CCCACCTTTGGATCACTGGA (SEQ ID NO: 35), and 5'-TCGTATGCTTGTCTTTTCCT (SEQ ID NO: 36); 16G, 5'-ACATGTGCCCGCTGTGCTCC (SEQ ID NO: 37), and 5'-GGGCCGAGGCCTCTCCTCAA (SEQ ID NO: 38); 16H, 5'-TGGAGGAGCCACGTCCCCAG (SEQ ID NO: 39), and 5'-GCGGGGCAGACCCTTCACAC (SEQ ID NO: 40); 16J, 5'-GCTGTGGTGGTGACTGGGGC (SEQ ID NO: 41), and 5'-CCAGGCGCGTGGATTTCCCA (SEQ ID NO: 42); 16K, 5'-TGGGGGCAGAAGCAGTCGGT (SEQ ID NO: 43), and 5'-GGCCTGTGGGTAGCCAGGGAT (SEQ ID NO: 44); β-actin, 5'-TGTGATGGTGGGAATGGGTCAG (SEQ ID NO: 45) and 5'-TTTGATGTCACGCACGATTTCC (SEQ ID NO: 46).

The mRNA was quantified at the point where Light Cycler System detected the upstroke of the exponential phase of PCR accumulation with the respective linearized plasmid DNA as reference.

Western Blotting

Cells were lysed in RIPA buffer [50 mM Hepes-NaOH buffer (pH 8.0) containing 1% NP-40, 0.1% SDS, 0.5% sodium deoxycholate, 150 mM NaCl, and protease inhibitor cocktail (cOmplete Mini, Roche Diagnostics)]. After removing debris, cell lysates were mixed with 5×SDS sample buffer [200 mM Tris-HCl (pH 6.8), 10% SDS, 25% glycerol, 5% β-mercaptoethanol, and 0.05% Bromophenolblue], incubated at room temperature for 30 min, and separated by 10% SDS-PAGE (Bio Craft, Tokyo, Japan). After transferring proteins to a PVDF membrane (Millipore, Billerica, Mass.), membranes were probed with HRP-conjugated mouse anti-FLAG M2 (Sigma-Aldrich, St. Louis, Mo.), and peroxidase activity was detected using a Western Lightning®-ECL system (PerkinElmer, Waltham, Mass.).

To prepare rabbit antibody against mouse TMEM16F, the N-terminal region of mouse TMEM16F (amino acids from 1-289) was fused to glutathione-S-transferase (GST) in a pGEX-5X-1 vector (GE Healthcare, Buckinghamshire, England). The recombinant protein was produced in *E. coli*, purified with Glutathione-Sepharose, and used to immunize rabbits at Takara Bio as a custom order. Western blotting with the rabbit anti-TMEM16F and HRP-labeled goat anti-rabbit Ig (Dako, Copenhagen, Denmark) was carried out as described above using Immunoreaction Enhancer Solution (Can Get Signal®, Toyobo Life Science, Tokyo, Japan).

Analysis of PS Exposure

The $Ca^{2+}$-induced PS exposure were examined as described (20). In brief, $5 \times 10^5$ cells were stimulated at 20° C. with 3.0 μM A23187 in 500 μl of 10 mM Hepes-NaOH buffer (pH 7.4) containing 140 mM NaCl, 2.5 mM $CaCl_2$ and 5 μg/ml Propidium Iodide (PI), and 1000-fold-diluted Cy5-labeled Annexin V (Bio Vision, Milpitas, Calif.), and applied to the injection chamber of a FACSAria (BD Bioscience, Franklin Lakes, N.J.) set at 20° C.

Internalization of NBD-PC and NBD-GalCer

Cells ($10^6$) were stimulated at 15° C. with 250 nM A23187 in 1 ml Hank's Balanced Salt Solution (HBSS) (Gibco, Billings, Mont.) containing 1 mM $CaCl_2$, with a fluorescent probe, 100 nM 1-oleoyl-2-{6-[(7-nitro-2-1,3-benzoxadiazol-4-yl)amino]hexanoyl}-sn-glycero-3-phosphocholine (NBD-PC) (Avanti Polar Lipids, Alabaster, Ala.), or 250 nM N-[6-[(7-nitro-2-1,3-benzoxadiazol-4-yl)amino]hexanoyl]-D-galactosyl-β1-1'-sphingosine (C6-NBD galactosyl ceramide or NBD-GalCer) (Avanti Polar Lipids). Aliquots (150 μl) were mixed with 150 μl HBSS containing 5 mg/ml fatty-acid free BSA (Sigma-Aldrich) and 500 nM Sytoxblue (Molecular Probes, Eugene, Oreg.), and analyzed by FACSAria.

Induction of Apoptosis

Apoptosis was induced with FasL as described (25). In brief, IFETs expressing mouse Fas were treated with 60 units/ml FasL at 37° C. for 2 h, and PS exposure was determined by flow cytometry with Cy5-Annexin V. To detect activated caspase 3, cells were fixed at 37° C. for 10 min in PBS containing 1% paraformaldehyde, permeabilized with 90% methanol at −20° C., and stained with rabbit mAb against active caspase 3 (Cell Signaling, Danvers, Mass.). Cells were then incubated with Alexa 488-labeled goat anti-rabbit IgG (Invitrogen), and analyzed by FACSAria.

Electrophysiology

TMEM16 sequences, FLAG-tagged at C-terminus, were inserted into pEF-BOS-EX (31). HEK293T cells ($2.5 \times 10^5$) were co-transfected with 1.0 μg of TMEM16 expression vector and 0.1 μg of pMAX-EGFP (Lonza Group, Basel, Switzerland) using FuGENE6 (Promega, Madison, Wis.). At 24 h after transfection, cells were re-seeded on glass coverslips coated with fibronectin (Sigma-Aldrich). Within 24 h after re-seeding, whole-cell recordings of cells expressing EGFP were performed using a patch-clamp amplifier (Axopatch 200B, Molecular Devices, Sunnyvale, Calif.) as described (23,32). The extracellular solution contained 140 mM NaCl, 5 mM KCl, 2 mM $CaCl_2$, 1 mM $MgCl_2$, 30 mM glucose, and 10 mM Hepes-NaOH (pH 7.4). The intracellular solution contained 140 mM NaCl, 1.12 mM EGTA, 1 mM $CaCl_2$, 30 mM glucose, and 10 mM Hepes-NaOH (pH7.4). The free $Ca^{2+}$ concentration (500 nM) was calculated with WEBMAXC software.

Results

Establishment of $TMEM16F^{-/-}$ Fetal Thymocyte Cell Lines $Ca^{2+}$-dependent PS exposure is reduced by knocking down TMEM16F mRNA and accelerated by TMEM16F overexpression, suggesting that TMEM16F is a phospholipid scramblase (20). To demonstrate TMEM16F's involvement in $Ca^{2+}$-dependent phospholipid scrambling and to determine whether TMEM16F plays a role in exposing PS to the cell surface during apoptotic cell death, we established from fetal thymus tissue a TMEM16F-deficient mouse cell line that expresses a small number of TMEM16 family members, including TMEM16F (see below).

Figure 1D:
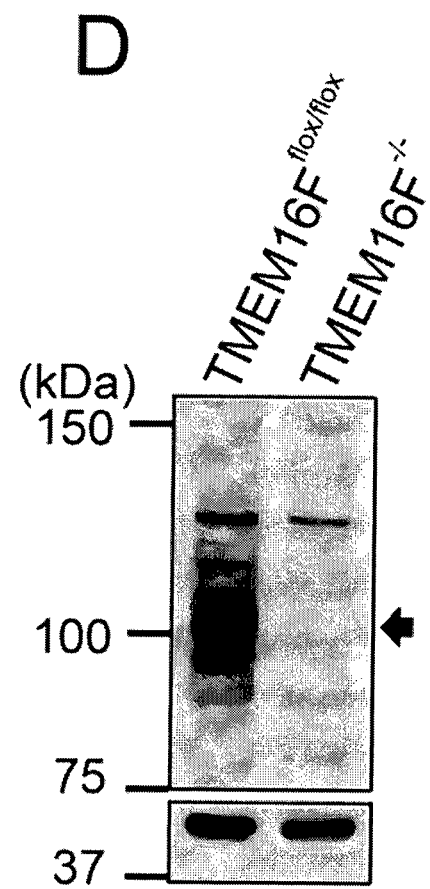

A targeting vector in which exon 2 of TMEM16F gene was flanked by loxP sequences was used to replace the TMEM16F allele in a mouse embryonic stem cell (ES) line from a C57BL/6 background (FIG. 1A). Mice carrying the floxed allele were generated from the ES clone, and intercrossed. Embryos were genotyped at embryonic day 14.5, and fetal $TMEM16F^{flox/flox}$ thymus cells were infected with a retrovirus carrying H-$ras^{V12}$ and c-myc to establish IFET cell lines. Flow cytometry analysis showed that IFETs expressed Thy-1 weakly and CD44 strongly, but did not express CD4 or CD8; this indicated that they were derived from a T-cell lineage at an early developmental stage. A real-time RT-PCR analysis showed that IFETs expressed TMEM16F, 16H and 16K (FIG. 1B). Next, IFETs were infected with adenovirus carrying the CRE recombinase gene, and cells missing exon 2 of the TMEM16F gene were cloned (FIG. 1C). Removing exon 2 causes a frame-shift and truncates TMEM16F protein at the N-terminal region. Accordingly, Western blotting with an anti-TMEM16F antibody showed broad bands around 120 kDa in TMEM16F$^{flox/flox}$ but not TMEM16F$^{-/-}$ IFETs (FIG. 1D). An apparent Mr of TMEM16F detected by SDS-PAGE is slightly larger than the expected Mr for TMEM16F (106 kDa), which may be explained by glycosylation, since mouse TMEM16F carry 6 putative N-glycosylation sites (Asn-X-Ser/Thr).

Requirement of TMEM16F for Ca$^{2+}$-Induced, but not Apoptotic PS-Exposure

Figure 2A:
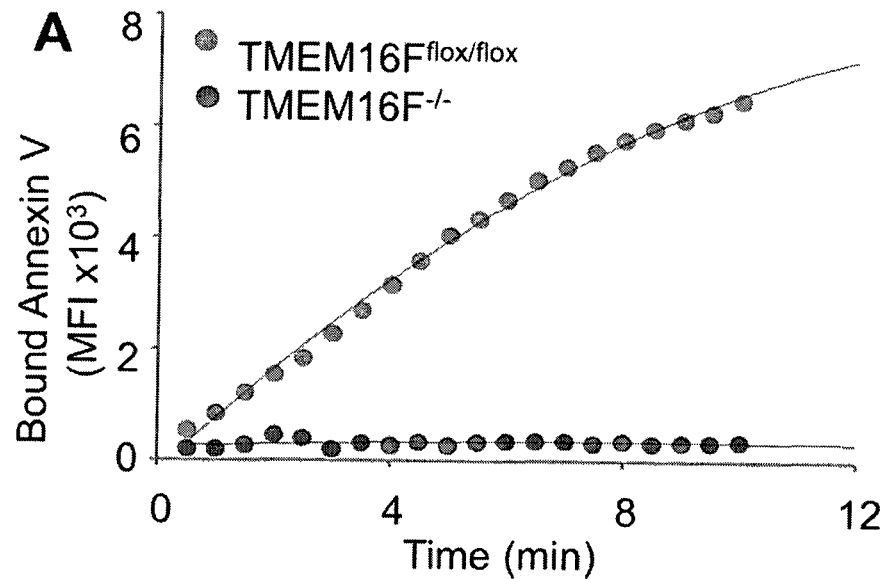
Figure 2B:
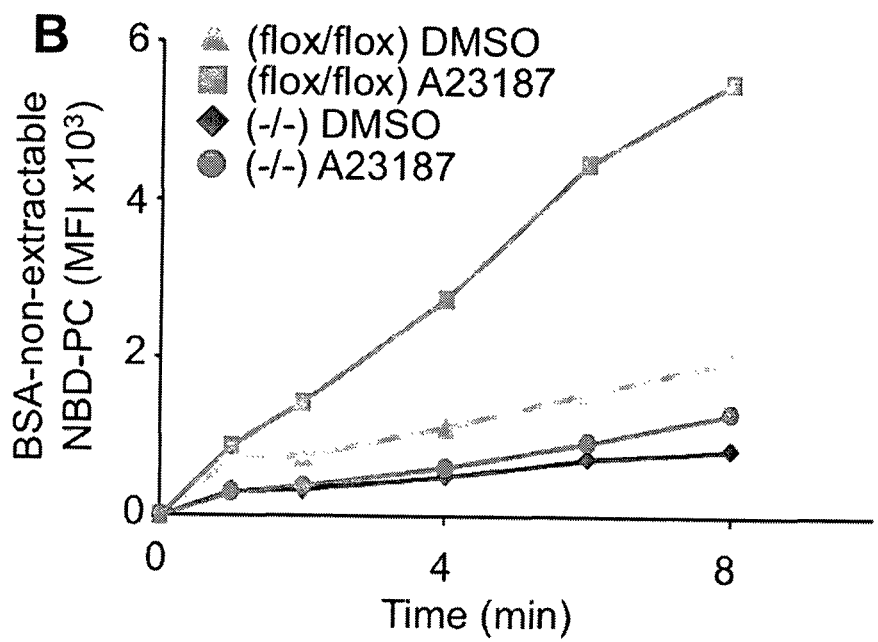
Figure 2C:
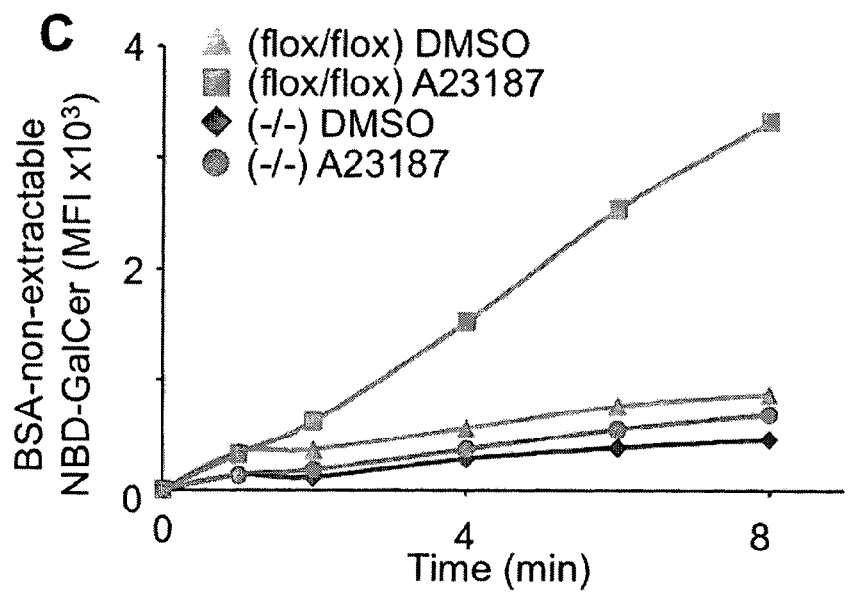

TMEM16F$^{flox/flox}$ IFETs treated at 20° C. with a Ca$^{2+}$ ionophore A23187 quickly exposed PS (FIG. 2A); however, this exposure was completely absent in TMEM16$^{-/-}$ IFETs. Similarly, the treatment of TMEM16F$^{flox/flox}$ but not TMEM16F$^{-/-}$ IFETs with A23187 caused rapid PE-exposure, detected by binding of RO-peptide (20) (data not shown). We then examined the role of TMEM16F in lipid internalization, and found that TMEM16F$^{flox/flox}$ but not TMEM16$^{-/-}$ IFETs internalized NBD-PC and NBD-GalCer upon Ca$^{2+}$-ionophore treatment (FIGS. 2B and 2C). These results indicated that TMEM16F is responsible for Ca$^{2+}$-dependent lipid scrambling in IFETs.

Figure 2D:
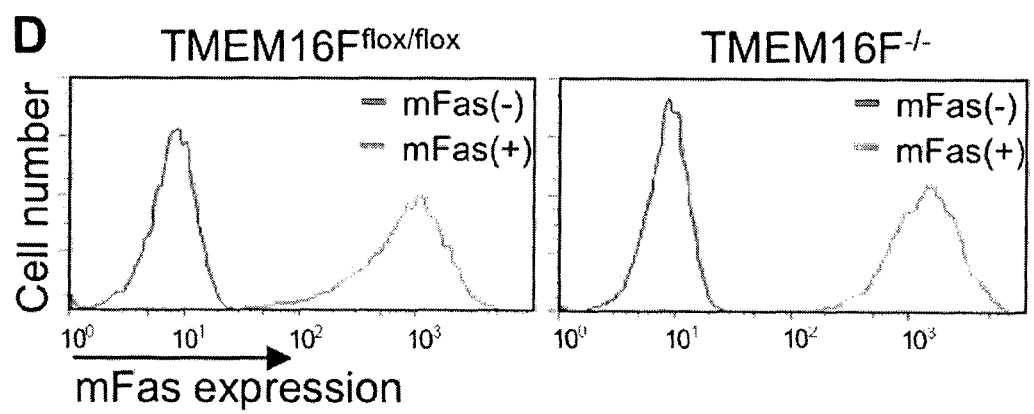
Figure 2E:
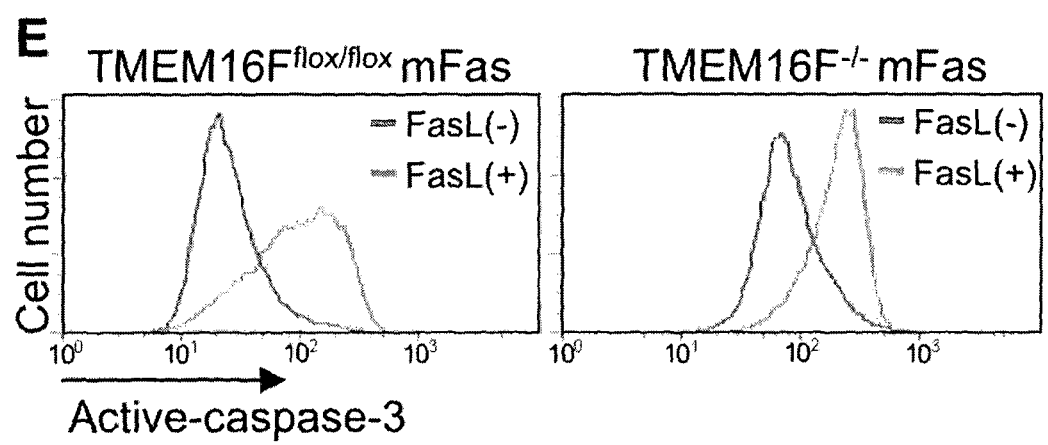
Figure 2F:
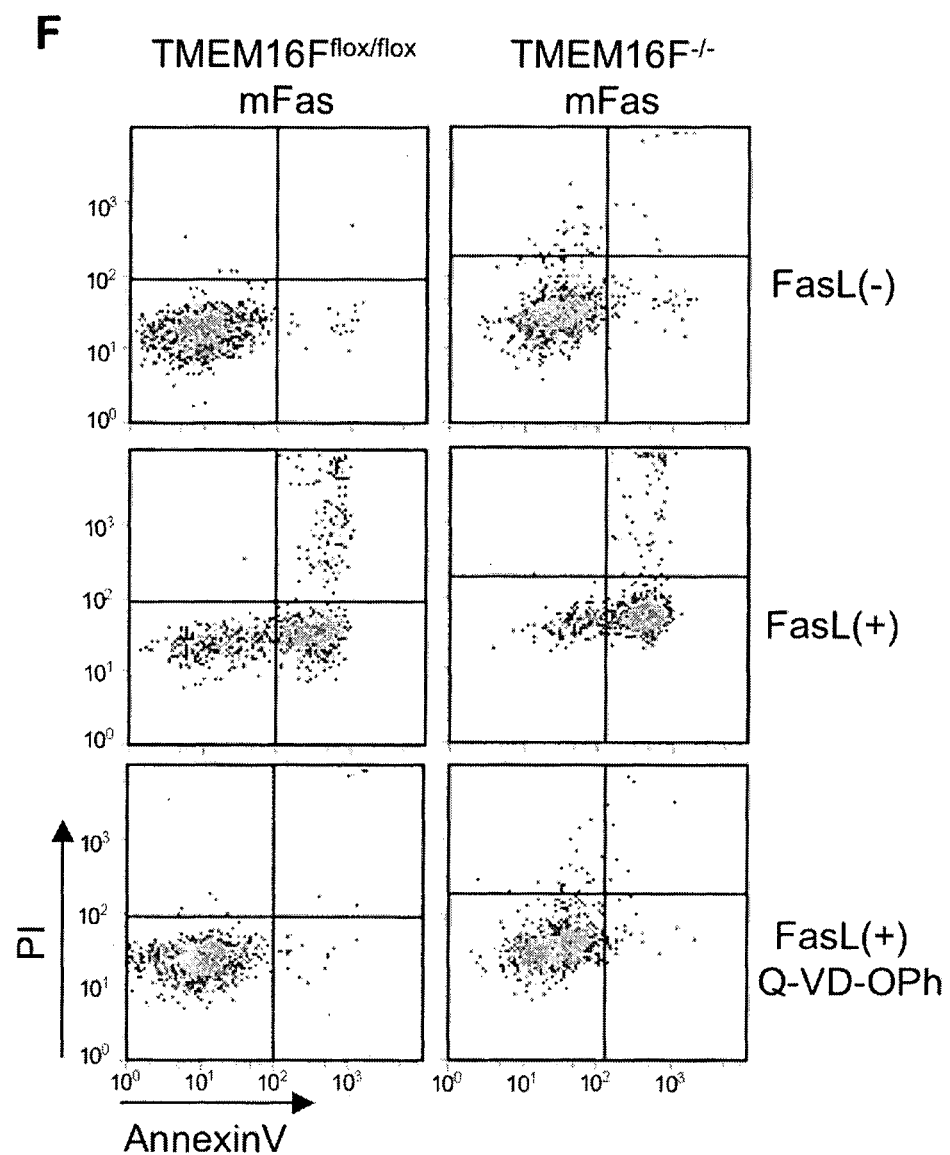
Figure 2G:
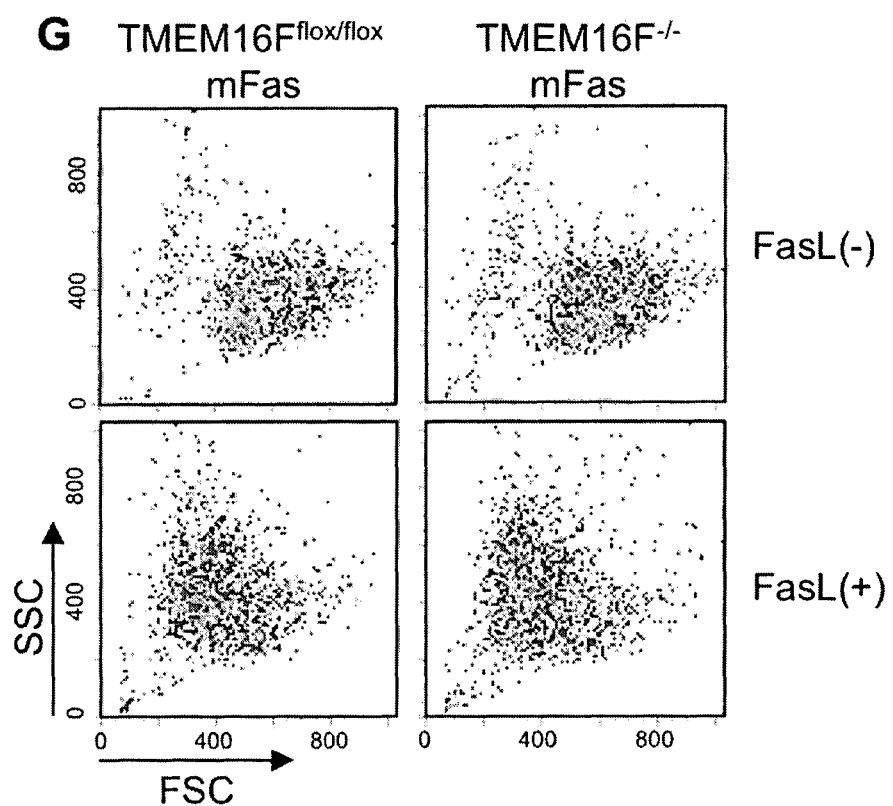

In agreement with previous report showing that Fas is not expressed in T cells at early developmental stages (33), IFETs do not express Fas (FIG. 2D). When IFETs were transformed with mouse Fas, FasL efficiently activated caspase 3 (FIG. 2E) and the cells quickly responded by exposing PS (FIG. 2F). A TMEM16F-null mutation did not affect either FasL-induced PS exposure or caspase activation (FIGS. 2E and 2F). In cells undergoing apoptosis, cell size decreases and cellular granularity increases (34). Treating the TMEM16F$^{flox/flox}$ and TMEM16F$^{-/-}$ IFETs with FasL decreased the cell size (forward-scattered light, FSC) and increased the cellular granularity (side-scattered light, SSC) to the same extent (FIG. 2G). Therefore, we concluded that caspase-dependent apoptotic PS exposure and cell shrinkage take place independently of TMEM16F.

TMEM16 Family Members' Abilities to Expose PS

The ten TMEM16 family members have similar topologies, and 20-60% amino acid sequence identity (35,36). To examine TMEM16 family members' ability to scramble phospholipids, we transformed TMEM16F F$^{-/-}$ IFETs, in which the Ca$^{2+}$-dependent lipid scramblase activity is completely lost, with mouse retroviral vectors carrying FLAG-tagged TMEM16 family members. Since the expression plasmids for TMEM16C, 16D, and 16E with their endogenous sequences produced very low protein levels in IFETs, their sequences were modified to optimize the mRNA stability and translation efficiency. Western blots with an anti-FLAG mAb detected a specific band for each TMEM16 family member (FIG. 3A). Except for TMEM16K, their apparent Mr, detected by SDS-PAGE, is larger than the calculated Mr, which may be explained by glycosylation because these members carry 1-6 N-glycosylation sites. On the other hand, the apparent Mr (65 kDa) of TMEM16K, that does not have a putative N-glycosylation site, was significantly smaller than its estimated Mr (76 kDa). Some membrane proteins are known to behave anomalously in SDS-PAGE (37), and TMEM16K may belong to the group of this category. The Western blots also showed that most of the TMEM16 family members were expressed at similar levels, except that the TMEM16E level was 3-5 times lower, and TMEM16K level 5-10 times higher than those of other family members (FIG. 3A). As expected, Ca$^{2+}$ ionophore treatment efficiently induced TMEM16F$^{-/-}$ IFET transformants expressing TMEM16F to expose PS (FIG. 3B). The TMEM16D—as well as TMEM16G and 16J—transformants also exposed PS upon Ca$^{2+}$-treatment, although the ability of TMEM16G, or 16J to enhance the PS exposure was weaker than that of TMEM16F and 16D. On the other hand, no or little PS-exposing activity was detected with TMEM16A, 16B, 16C, 16E, 16H and 16K. Similarly, TMEM16F$^{-/-}$ IFETs lost the ability to internalize NBD-PS, and this activity was rescued strongly by transforming the cells with TMEM16D, 16F, and 16J, and weakly by 16G. While, IFETs transformants expressing TMEM16C and 16E did not internalize NBD-PS (data not shown).

TMEM16 Family Members' Abilities to Scramble Lipids

TMEM16F scrambled not only PS and PE, but also other lipids (FIG. 2). To examine the lipid scramblase activity of other TMEM16 family members, TMEM16F$^{-/-}$ IFETs expressing TMEM16 family members were incubated with a fluorescent probe, NBD-PC or NBD-GalCer. As shown in FIG. 4A, the TMEM16F$^{-/-}$ IFETs expressing TMEM16D constitutively, or without A23187-treatment, internalized NBD-PC, and this internalization was strongly enhanced by the A23187 treatment. The A23187-induced NBD-PC uptake with the TMEM16D transformants was stronger than that observed with the 16F-transformants. Pre-treatment of TMEM16D-transformants with BAPTA-AM, a cell-permeable Ca$^{2+}$ chelator, reduced the NBD-PC uptake observed without Ca$^{2+}$-ionophore (FIG. 4B), suggesting that the endogenous cellular level of Ca$^{2+}$ is sufficient to activate the scrambling activity of TMEM16D. As with PS exposure, the A23187- treatment did not induce NBD-PC uptake in IFETs expressing TMEM16A, 16B, 16E, 16H, or 16K (FIG. 4A). However, cells expressing TMEM16C, 16G, or 16J did internalize NBD-PC when treated with Ca$^{2+}$ ionophore.

A similar result was obtained using NBD-GalCer as a substrate. When treated with A23187, TMEM16F$^{-/-}$ transformants expressing TMEM16F incorporated NBD-GalCer, but those expressing TMEM16A, 16B, 16E, 16H, or 16K did not (FIG. 4C). Cells expressing TMEM16D constitutively incorporated NBD-GalCer, and this uptake was enhanced by A23187 treatment. The cells expressing TMEM16C, 16G, or 16J also internalized NBD-GalCer, although TMEM16C's ability to internalize NBD-GalCer was weaker compared with others. These results suggested that TMEM16C, 16D, 16F, 16G and 16J scramble various phospholipids and glycosphingolipids with some different substrate preference.

Chloride Channel Activity of TMEM16 Family Members

TMEM16A and 16B are Ca$^{2+}$-dependent Cl$^-$ channels (22-24). To determine whether there are any other TMEM16 family Cl$^-$ channels, and whether the scramblase activity of TMEM16 family members depends on Cl$^-$-channel activity, human 293T cells were co-transfected with the TMEM16 expression plasmid and a vector expressing GFP (FIG. 5A). The Ca$^{2+}$-dependent chloride channel activity in GFP-positive cells was then determined by whole-cell patch clamp analysis (23). We chose 293T cell line as host cells because it has little Ca$^{2+}$-dependent Cl$^-$-channel activity (FIG. 5B) and was used successfully to show that TMEM16A and 16B act as Cl$^-$ channels (22-24).

In the patch-clamp analysis, increasing the intracellular free Ca$^{2+}$ in the pipette solution to 500 nM yielded large outward rectifying currents in cells expressing TMEM16A or 16B (FIGS. 5B and 5C). In contrast, other TMEM16 family members induced little if any Ca$^{2+}$-dependent current in 293T cells, and the effect of increasing the pipette solution Ca$^{2+}$ concentration from 500 nM to 5 μM was negligible (data not shown). Therefore, we concluded that within the TMEM16 family, only TMEM16A and 16B act as Ca$^{2+}$- dependent Cl⁻ channels, and that the phospholipid scrambling activity of TMEM16C, 16D, 16F, 16G, and 16J is independent of Cl⁻-channel activity.

Expression of TMEM16 Family Members in Mouse Tissues

Real-time PCR analysis of TMEM16 mRNA in various mouse tissues showed that each tissue expressed only a limited number of TMEM16 family members (FIG. 6). Of the two Cl⁻ channels of TMEM16 family, TMEM16A and 16B, we found that TMEM16B was strongly expressed in brain and eye tissues, but weakly expressed or absent in tissues where TMEM16A was strongly expressed, such as the pancreas, liver, salivary glands, stomach, lung, skin, and mammary glands. Of the 5 lipid scramblases of TMEM16 family, 16C, 16D, 16F, 16G and 16J, TMEM16F was ubiquitously expressed in various tissues. Whereas, other scramblases were present only in a few tissues: TMEM16C and 16J were strongly expressed in the brain and skin, respectively, while 16D was found at a low level in a few tissues such as the brain, ovary, heart, and eyes, and 16G and 16J were found in the stomach and intestines. Of the TMEM16 proteins that did not show scramblase or Cl⁻-channel activity, 16H and 16K were expressed ubiquitously in various tissues, while 16E was expressed only in the muscle and skin.

CITATION LIST

1. Balasubramanian, K., and Schroit, A. (2003) Aminophospholipid asymmetry: A matter of life and death, *Annu. Rev. Physiol.* 65, 701-734
2. van Meer, G., Voelker, D., and Feigenson, G. (2008) Membrane lipids: where they are and how they behave, *Nat. Rev. Mol. Cell Biol.* 9, 112-124
3. Nagata, S., Hanayama, R., and Kawane, K. (2010) Autoimmunity and the clearance of dead cells, *Cell* 140, 619-630
4. Zwaal, R. F., Comfurius, P., and Bevers, E. M. (1998) Lipid-protein interactions in blood coagulation, *Biochim. Biophys. Acta* 1376, 433-453
5. Boas, F. E., Forman, L., and Beutler, E. (1998) Phosphatidylserine exposure and red cell viability in red cell aging and in hemolytic anemia., *Proc. Natl. Acad. Sci. USA* 95, 3077-3081
6. Yoshida, H., Kawane, K., Koike, M., Mori, Y., Uchiyama, Y., and Nagata, S. (2005) Phosphatidylserine-dependent engulfment by macrophages of nuclei from erythroid precursor cells, *Nature* 437, 754-758
7. Sessions, A., and Horwitz, A. (1983) Differentiation-related differences in the plasma membrane phospholipid asymmetry of myogenic and fibrogenic cells, *Biochim. Biophys. Acta* 728, 103-111
8. Helming, L., and Gordon, S. (2009) Molecular mediators of macrophage fusion, *Trends Cell Biol.* 19, 514-522
9. Adler, R., Ng, A., and Rote, N. (1995) Monoclonal antiphosphatidylserine antibody inhibits intercellular fusion of the choriocarcinoma line, JAR, *Biol. Reprod.* 53, 905-910
10. Gadella, B., and Harrison, R. (2002) Capacitation induces cyclic adenosine 3',5'-monophosphate-dependent, but apoptosis-unrelated, exposure of aminophospholipids at the apical head plasma membrane of boar sperm cells, *Biol. Reprod.* 67, 340-350
11. Leventis, P. A., and Grinstein, S. (2010) The Distribution and Function of Phosphatidylserine in Cellular Membranes, *Annu. Rev. Biophys.* 39, 407-427
12. Folmer, D., Elferink, R., and Paulusma, C. (2009) P4 ATPases—lipid flippases and their role in disease, *Biochim. Biophys. Acta* 1791, 628-635
13. Oram, J., and Vaughan, A. (2000) ABCA1-mediated transport of cellular cholesterol and phospholipids to HDL apolipoproteins, *Curr. Opin. Lipidol* 11, 253-260
14. Williamson, P., Halleck, M., Malowitz, J., Ng, S., Fan, X., Krahling, S., Remaley, A., and Schlegel, R. (2007) Transbilayer phospholipid movements in ABCA1-deficient cells, *PLoS ONE* 2, e729
15. Bevers, E., and Williamson, P. (2010) Phospholipid scramblase: an update, *FEBS Lett.* 584, 2724-2730
16. Basse, F., Stout, J. G., Sims, P. J., and Wiedmer, T. (1996) Isolation of an erythrocyte membrane protein that mediates Ca2+-dependent transbilayer movement of phospholipid, *J. Biol. Chem.* 271, 17205-17210
17. Zhou, Q., Zhao, J., Stout, J., Luhm, R., Wiedmer, T., and Sims, P. (1997) Molecular cloning of human plasma membrane phospholipid scramblase. A protein mediating transbilayer movement of plasma membrane phospholipids, *J. Biol. Chem.* 272, 18240-18244
18. Zhou, Q., Zhao, J., Wiedmer, T., and Sims, P. J. (2002) Normal hemostasis but defective hematopoietic response to growth factors in mice deficient in phospholipid scramblase 1, *Blood* 99, 4030-4038
19. Sahu, S., Gummadi, S., Manoj, N., and Aradhyam, G. (2007) Phospholipid scramblases: an overview, *Arch. Biochem. Biophys.* 462, 103-114
20. Suzuki, J., Umeda, M., Sims, P. J., and Nagata, S. (2010) Calcium-dependent phospholipid scrambling by TMEM16F, *Nature* 468, 834-838
21. Castoldi, E., Collins, P. W., Williamson, P. L., and Bevers, E. M. (2011) Compound heterozygosity for 2 novel TMEM16F mutations in a patient with Scott syndrome, *Blood* 117, 4399-4400
22. Caputo, A., Caci, E., Ferrera, L., Pedemonte, N., Barsanti, C., Sondo, E., Pfeffer, U., Ravazzolo, R., Zegarra-Moran, O., and Galietta, L. (2008) TMEM16A, a membrane protein associated with calcium-dependent chloride channel activity, *Science* 322, 590-594
23. Schroeder, B., Cheng, T., Jan, Y., and Jan, L. (2008) Expression cloning of TMEM16A as a calcium-activated chloride channel subunit, *Cell* 134, 1019-1029
24. Yang, Y., Cho, H., Koo, J., Tak, M., Cho, Y., Shim, W., Park, S., Lee, J., Lee, B., Kim, B., Raouf, R., Shin, Y., and Oh, U. (2008) TMEM16A confers receptor-activated calcium-dependent chloride conductance, *Nature* 455, 1210-1215
25. Shiraishi, T., Suzuyama, K., Okamoto, H., Mineta, T., Tabuchi, K., Nakayama, K., Shimizu, Y., Tohma, J., Ogihara, T., Naba, H., Mochizuki, H., and Nagata, S. (2004) Increased cytotoxicity of soluble Fas ligand by fusing isoleucine zipper motif, *Biochem. Biophys. Res. Commun.* 322, 197-202
26. Morita, S., Kojima, T., and Kitamura, T. (2000) Plat-E: an efficient and stable system for transient packaging of retroviruses, *Gene Ther.* 7, 1063-1066
27. Kanki, H., Suzuki, H., and Itohara, S. (2006) High-efficiency CAG-FLPe deleter mice in C57BL/6J background, *Exp. Anim.* 55, 137-141
28. Imao, T., and Nagata, S. (2013) Apaf-1- and Caspase-8-independent apoptosis, *Cell Death Differ*
29. Akagi, T., Sasai, K., and Hanafusa, H. (2003) Refractory nature of normal human diploid fibroblasts with respect to oncogene-mediated transformation, *Proc. Natl. Acad. Sci. USA* 100, 13567-13572

30. Watson, J. D., Morrissey, P. J., Namen, A. E., Conlon, P. J., and Widmer, M. B. (1989) Effect of IL-7 on the growth of fetal thymocytes in culture, *J. Immunol.* 143, 1215-1222

31. Murai, K., Murakami, H., and Nagata, S. (1998) Myeloid-specific transcriptional activation by murine myeloid zinc finger protein-2, *Proc. Natl. Acad. Sci. USA* 95, 3461-3466

32. Kuba, H., Yamada, R., and Ohmori, H. (2003) Evaluation of the limiting acuity of coincidence detection in nucleus laminaris of the chicken, *J. Physiol.* 552, 611-620

33. Ogasawara, J., Suda, T., and Nagata, S. (1995) Selective apoptosis of CD4 CD8 thymocytes by the anti-Fas antibody, *J. Exp. Med.* 181, 485-491

34. Dive, C., Gregory, C. D., Phipps, D. J., Evans, D. L., Milner, A. E., and Wyllie, A. H. (1992) Analysis and discrimination of necrosis and apoptosis (programmed cell death) by multiparameter flow cytometry, *Biochim. Biophys. Acta* 1133, 275-285

35. Galietta, L. (2009) The TMEM16 protein family: a new class of chloride channels?, *Biophys. J.* 97, 3047-3053

36. Duran, C., and Hartzell, H. C. (2011) Physiological roles and diseases of tmem16/anoctamin proteins: are they all chloride channels?, *Acta Pharmacolgica Sinica* 31, 685-692

37. Rath, A., Glibowicka, M., Nadeau, V. G., Chen, G., and Deber, C. M. (2009) Detergent binding explains anomalous SDS-PAGE migration of membrane proteins., *Proc. Natl. Acad. Sci. USA* 106, 1760-1765

38. Segawa, K., Suzuki, J., and Nagata, S. (2011) Constitutive exposure of phosphatidylserine on viable cells, *Proc. Natl. Acad. Sci. USA* 108, 19246-19251

39. Williamson, P., Christie, A., Kohlin, T., Schlegel, R., Comfurius, P., Harmsma, M., Zwaal, R., and Bevers, E. (2001) Phospholipid scramblase activation pathways in lymphocytes, *Biochemistry* 40, 8065-8072

40. Schoenwaelder, S., Yuan, Y., Josefsson, E., White, M., Yao, Y., Mason, K., O'Reilly, L., Henley, K., Ono, A., Hsiao, S., Willcox, A., Roberts, A., Huang, D., Salem, H., Kile, B., and Jackson, S. (2009) Two distinct pathways regulate platelet phosphatidylserine exposure and procoagulant function, *Blood* 114, 663-666

41. Martins, J. R., Faria, D., Kongsuphol, P., Reisch, B., Schreiber, R., and Kunzelmann, K. (2011) Anoctamin 6 is an essential component of the outwardly rectifying chloride channel, *Proc. Nat. Acad. Sci. USA* 108, 18168-18172

42. Hampton, M., Vanags, D., Pörn-Ares, M., and Orrenius, S. (1996) Involvement of extracellular calcium in phosphatidylserine exposure during apoptosis, *FEBS Lett.* 399, 277-282

43. Hartzell, H. C., Yu, K., Xiao, Q., Chien, L. T., and Qu, Z. (2009) Anoctamin/TMEM16 family members are $Ca^{2+}$-activated $Cl^-$ channels, *J. Physiol.* 587, 2127-2139

44. Schreiber, R., Uliyakina, I., Kongsuphol, P., Warth, R., Mirza, M., Martins, J., and Kunzelmann, K. (2010) Expression and function of epithelial anoctamins, *J. Biol. Chem.* 285, 7838-7845

45. Duran, C., Qu, Z., Osunkoya, A. O., Cui, Y., and Hartzell, H. C. (2012) ANOs 3-7 in the anoctamin/Tmem16 Cl-channel family are intracellular proteins, *Am. J. Physiol. Cell Physiol.* 302, C482-493

46. Palmgren, M. G., and Nissen, P. (2011) P-type ATPases, *Annu. Rev. Biophys.* 40, 243-266

47. Chen, T.-Y., and Hwang, T.-C. (2008) CLC-0 and CFTR: chloride channels evolved from transporters, *Physiol. Rev.* 88, 351-387

48. Ferrera, L., Caputo, A., Ubby, I., Bussani, E., Zegarra-Moran, O., Ravazzolo, R., Pagani, F., and Galietta, L. (2009) Regulation of TMEM16A chloride channel properties by alternative splicing, *J. Biol. Chem.* 284, 33360-33368

49. Mizuta, K., Tsutsumi, S., Inoue, H., Sakamoto, Y., Miyatake, K., Miyawaki, K., Noji, S., Kamata, N., and Itakura, M. (2007) Molecular characterization of GDD1/TMEM16E, the gene product responsible for autosomal dominant gnathodiaphyseal dysplasia, *Biochem. Biophys. Res. Commun.* 357, 126-132

50. Bolduc, V., Marlow, G., Boycott, K., Saleki, K., Inoue, H., Kroon, J., Itakura, M., Robitaille, Y., Parent, L., Baas, F., Mizuta, K., Kamata, N., Richard, I., Linssen, W., Mahjneh, I., de Visser, M., Bashir, R., and Brais, B. (2010) Recessive Mutations in the Putative Calcium-Activated Chloride Channel Anoctamin 5 Cause Proximal LGMD2L and Distal MMD3 Muscular Dystrophies, *Am. J. Hum. Genet.* 86, 213-221

51. Tsutsumi, S., Kamata, N., Vokes, T., Maruoka, Y., Nakakuki, K., Enomoto, S., Omura, K., Amagasa, T., Nagayama, M., Saito-Ohara, F., Inazawa, J., Moritani, M., Yamaoka, T., Inoue, H., and Itakura, M. (2004) The novel gene encoding a putative transmembrane protein is mutated in gnathodiaphyseal dysplasia (GDD), *Am. J. Hum. Genet.* 74, 1255-1261

52. Vermeer, S., Hoischen, A., Meijer, R. P. P., Gilissen, C., Neveling, K., Wieskamp, N., de Brouwer, A., Koenig, M., Anheim, M., Assoum, M., Drouot, N., Todorovic, S., Milic-Rasic, V., Lochmuller, H., Stevanin, G., Goizet, C., David, A., Durr, A., Brice, A., Kremer, B., Warrenburg, B. P. C. v. d., Schijvenaars, M. M. V. A. P., Heister, A., Kwint, M., Arts, P., van der Wijst, J., Veltman, J., Kamsteeg, E.-J., Scheffer, H., and Knoers, N. (2010) Targeted Next-Generation Sequencing of a 12.5 Mb Homozygous Region Reveals ANO10 Mutations in Patients with Autosomal-Recessive Cerebellar Ataxia, *Am. J. Hum. Genet.* 87, 813-819

53. van den Eijnde, S., van den Hoff, M., Reutelingsperger, C., van Heerde, W., Henfling, M., Vermeij-Keers, C., Schutte, B., Borgers, M., and Ramaekers, F. (2001) Transient expression of phosphatidylserine at cell-cell contact areas is required for myotube formation, *J. Cell Sci.* 114, 3631-3642

54. Stowell, S. R., Karmakar, S., Arthur, C. M., Ju, T., Rodrigues, L. C., Riul, T. B., Dias-Baruffi, M., Miner, J., McEver, R. P., and Cummings, R. D. (2009) Galectin-1 induces reversible phosphatidylserine exposure at the plasma membrane, *Mol. Biol. Cell* 20, 1408-1418

55. Del Buono, B. J., White, S. M., Williamson, P. L., and Schlegel, R. A. (1989) Plasma membrane lipid organization and the adherence of differentiating lymphocytes to macrophages, *J. Cell. Physiol.* 138, 61-69

56. Fischer, K., Voelkl, S., Berger, J., Andreesen, R., Pomorski, T., and Mackensen, A. (2006) Antigen recognition induces phosphatidylserine exposure on the cell surface of human CD8+ T cells, *Blood* 108, 4094-4101

57. Ehlen, H. W., Chinenkova, M., Moser, M., Munter, H. M., Krause, Y., Gross, S., Brachvogel, B., Wuelling, M., Kornak, U., and Vortkamp, A. (2013) Inactivation of Anoctamin-6/Tmem16f, a regulator of phosphatidylserine scrambling in osteoblasts, leads to decreased mineral deposition in skeletal tissues, *J. Bone Miner. Res.* 28, 246-259

58. Charlesworth, G., Plagnol, V., Holmstrom, K. M., Bras, J., Sheerin, U.-M., Preza, E., Rubio-Agusti, I., Ryten, M., Schneider, S. A., Stamelou, M., Trabzuni, D., Abramov, A. Y., Bhatia, K. P., and Wood, N. W. (2012) Mutations in ANO3 cause dominant craniocervical dystonia: ion channel implicated in pathogenesis., Am. J. Hum. Genet. 91, 1041-1050
59. Kashyap, M. K., Marimuthu, A., Kishore, C. J. H., Peri, S., Keerthikumar, S., Prasad, T. S. K., Mahmood, R., Rao, S., Ranganathan, P., Sanjeeviah, R. C., Vijayakumar, M., Kumar, K. V. V., Montgomery, E. A., Kumar, R. V., and Pandey, A. (2009) Genomewide mRNA profiling of esophageal squamous cell carcinoma for identification of cancer biomarkers., Cancer Biol. Ther. 8, 36-46
60. Das, S., Hahn, Y., Nagata, S., Willingham, M., Bera, T., Lee, B., and Pastan, I. (2007) NGEP, a prostate-specific plasma membrane protein that promotes the association of LNCaP cells, Cancer Res 67, 1594-1601

The invention claimed is:

1. A method for screening an agent promoting or inhibiting a biological function of a transmembrane protein 16 (TMEM16) family member as a lipid scramblase, which comprises the following steps:

(1) treating TMEM16F deficient cells into which a gene encoding and expressing the TMEM16 family member selected from the group consisting of TMEM16C, TMEM16D, TMEM16G and TEMEM16J has been introduced with a candidate of the agent in the presence of $Ca^{2+}$, and (2) determining whether the candidate alters distribution of a lipid selected from the group consisting of phosphatidylserine, phosphatidylcholine, and galactosylceramide in plasma membrane of the cells, wherein a candidate which significantly increases distribution of phosphatidylserine in the outer leaflet of plasma membrane compared to control is selected as an agent promoting a biological function of the TMEM16 family member as a lipid scramblase, and a candidate significantly which decreases distribution of phosphatidylserine in the outer leaflet of plasma membrane compared to control is selected as an agent inhibiting a biological function of the TMEM16 family member as a lipid scramblase, and a candidate which significantly increases distribution of phosphatidylcholine or galactosylceramide in the inner leaflet of plasma membrane compared to control is selected as an agent promoting a biological function of the TMEM16 family member as a lipid scramblase, and a candidate which significantly decreases distribution of phosphatidylcholine or galactosylceramide in the inner leaflet of plasma membrane compared to control is selected as an agent inhibiting a biological function of the TMEM16 family member as a lipid scramblase; and wherein the cells are human, monkey, mouse, or rabbit cells, the distribution of phosphatidylserine in plasma membrane is determined by detecting the binding between phosphatidylserine exposed to the cell surface and an agent having phosphatidylserine-binding property, and the distribution of phosphatidylcholine or galactosylceramide in plasma membrane is determined by utilizing a fluorescently-labeled lipid.

2. The method of claim 1, wherein the lipid is selected from phosphatidylcholine or galactosylceramide when the TMEM16 family member is TMEM 16C.

3. The method of claim 1, wherein the lipid is selected from phosphatidylserine, phosphatidylcholine, or galactosylceramide when the TMEM16 family member is TMEM 16D.

4. The method of claim 1, wherein the lipid is selected from phosphatidylserine, phosphatidylcholine, or galactosylceramide when the TMEM16 family member is TMEM 16G.

5. The method of claim 1, wherein the lipid is selected from phosphatidylserine, phosphatidylcholine, or galactosylceramide when the TMEM16 family member is TMEM 16J.

* * * * *

SEQUENCE LISTING

```
<160> NUMBER OF SEQ ID NOS: 46

<210> SEQ ID NO 1
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 1
atatggatcc accatgaggg tccccgagaa gta                             33

<210> SEQ ID NO 2
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 2
atatgaattc cagcgcgtcc ccatggtact                                 30

<210> SEQ ID NO 3
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 3
atatgaattc cgcatgcact ttcacgacaa cca                             33

<210> SEQ ID NO 4
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 4
atatgaattc tacattggtg tgctgggacc                                 30

<210> SEQ ID NO 5
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 5
atatggatcc aaaatggtcc accactcagg ctc                             33

<210> SEQ ID NO 6
<211> LENGTH: 30
<212> TYPE: DNA
<213> ORGANISM: Artificial Sequence
```

-continued

```
<220> FEATURE:
<223> OTHER INFORMATION: Primer designated for PCR

<400> SEQUENCE: 6
atatcaattg aggccattca tggtgaatag                                        30

<210> SEQ ID NO 7
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 7
atatagatct aaaatggagg ccagctcttc tgg                                    33

<210> SEQ ID NO 8
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 8
atatcaattg tggccactca ttgtgatgtg                                        30

<210> SEQ ID NO 9
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 9
atatggatcc gagatggtgg agcaggaagg ctt                                    33

<210> SEQ ID NO 10
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 10
atatcaattg gactgtagtt ttagccttca                                        30

<210> SEQ ID NO 11
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 11
atatagatct gacatgctgc gggggcaagc gcg                                    33

<210> SEQ ID NO 12
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 12
atatgaattc gcctccggta accctactg                                         30
```

<210> SEQ ID NO 13
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 13
atatagatct gccatggccg aggcggcttc ggg                         33

<210> SEQ ID NO 14
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 14
atatgaattc aggcctgtga cctgcgtcct                             30

<210> SEQ ID NO 15
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 15
atatgaattc agcatgcagg atgatgagag ttc                         33

<210> SEQ ID NO 16
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 16
atatcaattg tacatccgtg ctcctggaac                             30

<210> SEQ ID NO 17
<211> LENGTH: 33
<212> TYPE: DNA
<213> ORGANISM: Artificial Sequence
<220> FEATURE:
<223> OTHER INFORMATION: Primer designated for PCR

<400> SEQUENCE: 17
atatggatcc aagatgagag tgactttatc aac                         33

<210> SEQ ID NO 18
<211> LENGTH: 30
<212> TYPE: DNA
<213> ORGANISM: Artificial Sequence
<220> FEATURE:
<223> OTHER INFORMATION: Primer designated for PCR

<400> SEQUENCE: 18
atatcaattg ggtagcttcc ttcccatctt                             30

<210> SEQ ID NO 19
<211> LENGTH: 2977
<212> TYPE: DNA
<213> ORGANISM: Artificial Sequence
<220> FEATURE:
<223> OTHER INFORMATION: The designed nucleotide sequence for mouse

TMEM16C

<400> SEQUENCE: 19

```
ggcgcgccgg atccgccacc atggtgcacc acagcggcag catccagagc ttcaagcagc      60
agaaaggcat gaacatcagc aagagcgaga tcaccaccga ggccagcctg aagcccagca     120
gaagaagcct gccctgcctg cccagagct acgcccacag caagagcctg agccagagcg     180
ccagcctgtt ccagagcacc gagagcgaga ccaggcccc taccagcgtg accttcctga     240
gcgccgacaa gcccgagcac gtgaccagcg aggaaagcag aaaggacagc accctgaagt     300
gcagcttcgc cgacctgagc gacttctgtc tggccctggg caaggacaag gactacctgg     360
acgagagcga gcacgccaac tacgacagaa gcagactgct gaacgacttc gtgaccaagg     420
acaagcccgc cagcaagacc aagctgagca gaacgacat gagctatatc gccagcagcg     480
gcctgctgtt caaggacggc aagaagagaa tcgactacat cctggtgtac cgcaagacca     540
acatccagta cgacaagagg aacaccttcg agaagaacct gagagccgag ggcctgatgc     600
tggaaaaaga gcccgctatc gccaaccccg acatcatgtt tatcaagatc cacatcccct     660
gggacaccct gtgcaaatac gccgagagac tgaacatcag ggtgcccttc cggaagaagt     720
gctactacac cgaccagaag aacaagagca gagcagggt gcagaactac ttcaagcgga     780
tcaagaaatg gatgagccag aaccccatgg tgctggacaa gagcgccttc cccgagctgg     840
aagagagcga ctgctacacc ggccccttca gcagagccaa atccaccac ttcatcatca     900
acaacaagga caccttcttc agcaacgcca ccagatccag aatcgtgtac cacatgctgg     960
aacggactaa gtacgagaac ggcatcagca agtgggcat cagaaagctg atcaccaacg    1020
gctcctatat cgccgccttc ccaccccacg agggcgccta caagagcagc ctgcccatca    1080
agacccacgg ccccccagaac aacagacatc tgctgtacga gagtgggcc agatggggaa    1140
tgtggtacaa gcaccagccc ctggacctga tcagaatgta cttcggcgag aagatcggcc    1200
tgtacttcgc ctggctgggc tggtacaccg gcatgctgat ccctgccgcc gtcgtgggcc    1260
tgtgcgtgtt cttctacggc ctggtcacca tgaacgagtc ccaggtgtcc caggaaatct    1320
gcaaggccac cgaggtgttc atgtgccccc tgtgcgacaa gaactgcagc ctgcagaggc    1380
tgaacgacag ctgcatctac gccaaagtga cctacctgtt cgacaacggc ggcaccgtgt    1440
tcttcgccat cttcatggct atctgggcta ccgtgttcct ggaatttgg aagagaaggc    1500
ggagcatcct gacctacacc tgggacctga tcgagtggga ggaagaggaa gagacactga    1560
ggccccagtt cgaggccaag tactacagaa tggaagtgat caaccccatc accggcaagc    1620
ctgagcccca ccagcccagc agcgacaaag tgaccagact gctggtgtcc gtgtccggca    1680
tcttcttcat gatcagcctg gtcatcaccg ccgtgttcgc cgtggtggtg tacagactgg    1740
tggtcatgga acagttcgcc agcttcaagt ggaacttcgt gaagcagcac tggcagttcg    1800
ccaccagcgg agccgccgtg tgcatcaact ttatcatcat catgctgctg aacctggcct    1860
atgagaagat cgcctacctg ctgaccaacc tggaataccc cagaaccgag tccgagtggg    1920
agaacagctt cgccctgaag atgttcctgt ccagttcgt gaacctgaac agctctatct    1980
tctatatcgc cttcttcctg ggccgcttcg tgggccaccc cggcaagtac aacaagctgt    2040
cgagaggtg gcggctggaa gagtgccacc ccagcggctg cctgatcgac ctgtgcctgc    2100
agatgggcgt gatcatgttc ctgaagcaga tttggaacaa cttcatggaa ctgggctacc    2160
ccctgatcca gaactggtgg tccagacaca agatcaagag aggcatccag gacgccagca    2220
tccccccagtg ggagaatgac tggaacctgc agcccatgaa catccacggc ctgatggacg    2280
```

```
agtacctgga aatggtgctg cagttcggct tcaccaccat cttcgtggcc gctttccccc    2340
tggcccctct gctggccctg ctgaacaaca tcatcgagat cagactggac gcctacaagt    2400
tcgtgaccca gtggcggagg cccctgcctg ccagagccac agacatcggc atctggctgg    2460
gcatcctgga aggcatcgga atcctggccg tgatcacaaa cgccttcgtg atcgccatca    2520
ccagcgatta catcccccgc ttcgtgtacg agtataagta cggcccctgc gccaaccacg    2580
tgaagcagaa cgagaactgc ctgaagggct acgtgaacaa cagcctgagc ttcttcgacc    2640
tgtccgagct gggcatgggc aagagcggct actgcagata cagagactac agaggccccc    2700
cttggagcag caagccctac gagttcaccc tgcagtactg gcacatcctg gccgccagac    2760
tggccttcat catcgtgttc gagcacctgg tgttcggcat caagtccttc attgcctacc    2820
tgatccccga catccccaag ggcctgagag agagaatcag acgcgagaag tacctggtgc    2880
aggaaatgat gtacgaggct gagctggaac atctgcagca gcagagaaga aagagcggcc    2940
agcccatcca ccacgagtgg cctgaattct taattaa                             2977

<210> SEQ ID NO 20
<211> LENGTH: 2899
<212> TYPE: DNA
<213> ORGANISM: Artificial Sequence
<220> FEATURE:
<223> OTHER INFORMATION: The designed nucleotide sequence for mouse
      TMEM16D

<400> SEQUENCE: 20
ggcgcgccgg atccgccacc atggaagcca gcagcagcgg catcaccaac ggcaagaaca      60
aggtgttcca cgccgagggc ggcctggacc tgcagagcca ccagctggac atgcagatcc     120
tgcccgacgg ccccaagagc gacgtggact tcagcgagat cctgaacgcc atccaggaaa     180
tggccaagga cgtcaacatc ctgttcgacg agctggaagc cgtgaacagc ccctgcaagg     240
acgacgacag cctgctgcac cccggcaacc tgaccagcac cagcgaggac accagcagac     300
tggaagctgg cggcgagaca gtgcgcgaga gaaacaagag caacggcctg tacttcaggg     360
acggcaagtg cagaatcgac tacatcctgg tgtacagaaa gagcaacccc cagaccgaga     420
agagagaggt gttcgagagg aacatcagag ccgagggcct gcagatggaa aaagagagca     480
gcctgatcaa cagcgacatc atcttcgtga agctgcacgc ccctgggag gtgctgggca     540 gatacgccga gcagatgaac gtgcggatgc ccttcagacg gaaaatctac tacctgccca     600
ggcggtacaa gttcatgagc aggatcgaca agcagatcag caggttcaga cggtggctgc     660
ccaagaaacc catgagactg gacaaagaga cactgcccga cctggaagag aacgactgct     720
acaccgcccc cttcagccag cagagaatcc accacttcat catccacaac aaggacacat     780
tcttcaacaa cgccaccaga tccaggatcg tgcaccacat cctgcagagg attaagtacg     840
aggaagggaa gaacaagatc ggcctgaaca gactgctgac caacggcagc tacgaggccg     900
ccttcccact gcacgagggc agctacagaa gcaagaacag catcaagacc cacggcgctg     960
tgaaccacag acatctgctg tacgagtgct gggccagctg gggcgtgtgg tacaagtacc    1020
agcccctgga cctcgtgcgg agatacttcg gcgagaagat cggactgtac ttcgcctggc    1080
tgggctggta caccggcatg ctgttccctg ccgcctttat cggcctgttc gtgttcctgt    1140
acggcgtgac caccctggac cactgccagg tgtccaaaga agtgtgccag gccaccgaca    1200
tcatcatgtg cccccgtgtgc gacaagtact gccccttcat gagactgagc gacagctgcg    1260
tgtacgccaa agtgacccac ctgttcgaca acggcgccac cgtgttcttc gccgtgttca    1320
```

```
tggccgtgtg ggctaccgtg ttcctggaat tttggaagag gcggagagcc gtgatcgcct    1380
acgactggga cctgatcgac tgggaggaag aagaggaaga gatccggccc cagttcgagg    1440
ccaagtacag caagaaagaa cggatgaacc ccatcagcgg caagcccgag ccctaccagg    1500
ccttcaccga caagtgcagc agactgatcg tgtccgccag cggcatcttc ttcatgatct    1560
gcgtcgtgat cgccgccgtg ttcggcatcg tgatctacag agtggtcacc gtgtccacct    1620
tcgccgcctt caagtgggcc ctgatcagaa acaacagcca ggtggccacc accggcaccg    1680
ccgtgtgtat caacttctgc atcatcatgc tgctgaacgt cctgtacgag aaggtggccc    1740
tgctgctgac aaacctggaa cagcccgaaa ccgagagcga gtgggagaac agcttcaccc    1800
tgaagatgtt tctgtttcag ttcgtgaacc tgaacagctc taccttctat atcgccttct    1860
tcctgggacg gttcaccggc caccctggcg cctacctgag actgatcaac cggtggcggc    1920
tggaagagtg ccaccccagc ggctgcctga tcgacctgtg catgcagatg ggcatcatta    1980
tggtcctgaa gcagacctgg aacaacttca tggaactggg ctaccccctg atccagaact    2040
ggtggaccag acggaaagtg cggcaggaac acggcaccga gagaaagatc aacttccccc    2100
agtgggagaa ggactacaac ctgcagccca tgaacgccta cggcctgttt gacgagtacc    2160
tggaaatgat cctgcagttc ggcttcacca ccatcttcgt ggccgctttc ccctggcccc    2220
ccctgctggc tctgctgaac aacatcatcg agatcagact ggacgcctac aagttcgtga    2280
cccagtggcg gaggcccctg gctagcagag ccaaggacat cggcatttgg tacggcatcc    2340
tggaaggcat cggcatcctg agcgtgatca ccaacgcctt cgtgatcgct atcaccagcg    2400
acttcatccc cagactggtg tacgcctata gtacggccc ctgtgctggc cagggcgagg    2460
ctggacagaa atgcatggtc ggatacgtga acgccagcct gagcgtgttc agaatcagcg    2520
acttcgagaa cagaagcgag cccgagagcg acggcagcga gttcagcggc accccctga    2580 agtactgcag atacagagac tacagggacc ccccccacag cctggcccct tacggctaca    2640
ccctgcagtt ctggcacgtg ctggccgcca gactggcctt catcatcgtg ttcgagcacc    2700
tggtgttctg catcaagcac ctgatcagct acctgatccc cgacctgccc aaggacctga    2760
gagacagaat gcggagagag aagtacctga ttcaggaaat gatgtacgag gccgagctgg    2820
aaagactgca gaaagagcgc aaagagcgga agaagaacgg caaggcccac cacaacgagt    2880
ggcccgaatt cttaattaa                                                 2899
```

<210> SEQ ID NO 21
<211> LENGTH: 2746
<212> TYPE: DNA
<213> ORGANISM: Artificial Sequence
<220> FEATURE:
<223> OTHER INFORMATION: The designed nucleotide sequence for mouse
       TMEM16E

<400> SEQUENCE: 21

```
ggcgcgccgg atccgccacc atggtcgaac aggaaggcct gaccgccaaa gagatcgact      60
acgccttcca gcagaacgag aacctgggca gcaaagagac aagcttcctg atccccgagg     120
acctgcagag cccccctgag aagagattca acctgttcct gagaaggcgg ctgatgttcc     180
agagaagcga gcacagcaag gacagcgtgt tcttcaggga cggcatcaga cagatcgact     240
tcgtgctgag ctacgtcgag gatctgaaga aggacggcga gctgaaggcc gagagaagaa     300
gagagttcga gcagaacctg agaaagaccg gcctggacct ggaaaccgag gacaagctga     360
acagcgagga cggcaagacc tacttcgtga agatccacgc cccctgggag gtgctggtca     420
```

```
catacgctga agtgctgggc atcaagatgc ctatcaagct gagcgacatc cccagaccca      480
agtacccccc cctgtcctac atgctgggcg ccgtgaagct gcccagcagc gtgaagtacc      540
ctacccccga gtacttcacc gcccagttca gcagacacag acaggaactg tttctgatcg      600
aggacgaggc cacattcttc ccaagcagca ccagaaaccg gatcgtgtac tacatcctga      660
gcagatgccc cttcggcgtg aagagggca agaagaagat cggcatcgag agactgctca       720
acagcaacac ctacctgagc gcctacccc tgcacgacgg acagtactgg aagcccagca       780
agaccaccag gcccaacgag aggtacaacc tgtgcaagaa ctgggccaga ttcagctact      840
tctacaaaga gcagcccttc cacctgatcc ggaactactt cggcgaaaag atcgggatct      900
actttgtgtt cctgggctac tacaccgaga tgctgctgtt cgccgccctc gtgggactgg      960
cctgcttcat ctacgcctg ctgagcatgg aaaacaacag aaccagcacc gaaatctgcg       1020
accccgacat cggcggccag atgatcatgt gccccctgtg cgacgaagtg tgcgactact      1080
ggcggctgaa caccacctgt ctgcactcca agttcagcca cctgttcgat aacgagagca      1140
cagtgttctt cgccctgttc atgggaatct gggtcaccct gttcctcgaa ttttggaagc      1200
agagacaggc cagactggaa tacgagtggg acctggtgga cttcgaggaa gaacagcagc      1260
agctgcagct cagacccgag ttcgaggcca tgtgcaagca caagaaaatg aaccccgtga      1320
ccaaagaaat ggaaccccac atgccccgt gccacagaat cccttggtac ttcgtgtccg       1380
gcaccaccgt gaccttcggc atggctctgc tgctgagtag catggtgtcc atcctgatct      1440
acagactgag cgtgttcgcc accttcgcca gcttcatgga aagcgaggcc accctgcagt      1500
ccgtgaagag tttcttcaca ccccagctgg ccaccgccct gagcggctct tgcctgaact      1560
gcatcgtgat cctgatcctc aacttcttct acgagaagat cagcgcctgg atcaccaaga      1620
tggaaatccc tagaacccac caggaatatg agagcagcct gaccctgaag atgttcctgt      1680
tccagttcgt gaactactac agctcctgct tctacgtggc cttcttcaag ggcaagttcg      1740
tgggctaccc cggcagctac acctacatgt tcaacatctg gcggagcgag gaatgcggcc      1800
ctgccggctg tctgatcgaa ctgaccaccc agctgaccat catcatgatc ggcaagcaga      1860
ttttcggcaa catccacgag gctttccagc ccctgatctt taactggtgg cgcagaagaa      1920
gggccagaac ccacagcgag aagctgtact ccagatggga gcaggaccac gacctccagg      1980
tgtacggcca cagaggcctg ttctacgagt atctggaaac agtgatccag ttcggcttcg      2040
ccacactgtt cgtggctagc ttccccctgg ccctctgtt cgccctgatg aacaacatca       2100
tgggcatcag agtggacgcc tggaagctga ccacacagta cagacggccc gtggccgcca      2160
aggctcactc tattggcgtg tggcaggaca tcctgtttgg catggccatc gtgtccgtgg      2220
ccaccaacgc cttcatcgtg tctttcacca gcgacatcat cccaggctg gtgtacttct      2280 acgcctacag caccaacagc accgagcccc tgtccggcta cgtgaacaac agcctgtccg      2340
tgttcctgat cgctgacttc cccaaccaca ccgtgcccat ggaaaagaaa gacttcgtga      2400
cctgccggta cagggactac agatacccc ccgaccacga ggataagtac agccacaaca      2460
tgcagttttg gcacgtgctg gccgctaaga tgaccttcat catcgtgatg gaacacgtgg      2520
tgtttctgtt caagttcctg ctggcctggc tgatccctga cgtgcccaag gacgtggtgg      2580
aaaagatcaa gagggaaaag ctgatgacca tcaagatcat ccacgatttc gagctgaaca      2640
agctcaaaga gaatctggac gtcgagtacg ggaacatcat gaagaacgtg ctggtggacg      2700
aggacaactc cctgaaggcc aagaccacag tggaattctt aattaa                    2746
```

<210> SEQ ID NO 22
<211> LENGTH: 24
<212> TYPE: DNA
<213> ORGANISM: Artificial Sequence
<220> FEATURE:
<223> OTHER INFORMATION: Primer designated for PCR

<400> SEQUENCE: 22
ctccagagtt tgtaagtaac acat                                              24

<210> SEQ ID NO 23
<211> LENGTH: 24
<212> TYPE: DNA
<213> ORGANISM: Artificial Sequence
<220> FEATURE:
<223> OTHER INFORMATION: Primer designated for PCR

<400> SEQUENCE: 23
cagtcatcga tgaattcata actt                                              24

<210> SEQ ID NO 24
<211> LENGTH: 25
<212> TYPE: DNA
<213> ORGANISM: Artificial Sequence
<220> FEATURE:
<223> OTHER INFORMATION: Primer designated for PCR

<400> SEQUENCE: 24
aagactgatt tccaaggtta tcgaa                                             25

<210> SEQ ID NO 25
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 25
accccgacgc cgaatgcaag                                                   20

<210> SEQ ID NO 26
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 26
gctggtcctg cctgacgctg                                                   20

<210> SEQ ID NO 27
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 27
gaggcgcaca cctgggtcac                                                   20

<210> SEQ ID NO 28
<211> LENGTH: 20
<212> TYPE: DNA
<213> ORGANISM: Artificial Sequence
<220> FEATURE:
<223> OTHER INFORMATION: Primer designated for PCR

```
<400> SEQUENCE: 28
atggggcgtg gatccggaca                                            20

<210> SEQ ID NO 29
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 29
gccagcaatt gccaacccccg                                           20

<210> SEQ ID NO 30
<211> LENGTH: 22
<212> TYPE: DNA
<213> ORGANISM: Artificial Sequence
<220> FEATURE:
<223> OTHER INFORMATION: Primer designated for PCR

<400> SEQUENCE: 30
gcagtccgac tcctccagct ct                                         22

<210> SEQ ID NO 31
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 31
acaggcatgc tcttccccgc                                            20

<210> SEQ ID NO 32
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 32
gcgatcactg ctcggcgtct                                            20

<210> SEQ ID NO 33
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 33
agcagctcca gcttcggcct                                            20

<210> SEQ ID NO 34
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 34
ttcacgctct gcagggtggc                                            20

<210> SEQ ID NO 35
```

```
<210> SEQ ID NO 35
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 35
cccacctttg gatcactgga                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 36
tcgtatgctt gtcttttcct                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 37
acatgtgccc gctgtgctcc                                                   20

<210> SEQ ID NO 38
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 38
gggccgaggc ctctcctcaa                                                   20

<210> SEQ ID NO 39
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 39
tggaggagcc acgtccccag                                                   20

<210> SEQ ID NO 40
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 40
gcggggcaga cccttcacac                                                   20

<210> SEQ ID NO 41
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 41
```

```
gctgtggtgg tgactggggc                                               20

<210> SEQ ID NO 42
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 42
ccaggcgcgt ggatttccca                                               20

<210> SEQ ID NO 43
<211> LENGTH: 20
<212> TYPE: DNA
<213> ORGANISM: Artificial Sequence
<220> FEATURE:
<223> OTHER INFORMATION: Primer designated for PCR

<400> SEQUENCE: 43 tggggggcaga agcagtcggt                                              20

<210> SEQ ID NO 44
<211> LENGTH: 21
<212> TYPE: DNA
<213> ORGANISM: Artificial Sequence
<220> FEATURE:
<223> OTHER INFORMATION: Primer designated for PCR

<400> SEQUENCE: 44
ggcctgtggg tagccaggga t                                             21

<210> SEQ ID NO 45
<211> LENGTH: 22
<212> TYPE: DNA
<213> ORGANISM: Artificial Sequence
<220> FEATURE:
<223> OTHER INFORMATION: Primer designated for PCR

<400> SEQUENCE: 45
tgtgatggtg ggaatgggtc ag                                            22

<210> SEQ ID NO 46
<211> LENGTH: 22
<212> TYPE: DNA
<213> ORGANISM: Artificial Sequence
<220> FEATURE:
<223> OTHER INFORMATION: Primer designated for PCR

<400> SEQUENCE: 46
tttgatgtca cgcacgattt cc                                            22
```